(12) United States Patent
Strother et al.

(10) Patent No.: US 8,086,318 B2
(45) Date of Patent: *Dec. 27, 2011

(54) PORTABLE ASSEMBLIES, SYSTEMS, AND METHODS FOR PROVIDING FUNCTIONAL OR THERAPEUTIC NEUROSTIMULATION

(75) Inventors: Robert B. Strother, Willoughby Hill, OH (US); Geoffrey B. Thrope, Shaker Heights, OH (US); Steven M. Galecki, Concord, OH (US); Joseph J. Mrva, Euclid, OH (US); Danny R. Pack, Avon Lake, OH (US)

(73) Assignee: NDI Medical, LLC, Cleveland, OH (US)

( * ) Notice: Subject to any disclaimer, the term of this patent is extended or adjusted under 35 U.S.C. 154(b) by 1316 days.

This patent is subject to a terminal disclaimer.

(21) Appl. No.: 11/595,556

(22) Filed: Nov. 10, 2006

(65) Prior Publication Data

US 2007/0123952 A1    May 31, 2007

Related U.S. Application Data

(63) Continuation-in-part of application No. 11/056,591, filed on Feb. 11, 2005, now Pat. No. 7,376,467, and a continuation-in-part of application No. 10/777,771, filed on Feb. 12, 2004, now Pat. No. 7,120,499.

(60) Provisional application No. 60/801,315, filed on May 18, 2006, provisional application No. 60/551,945, filed on Mar. 10, 2004.

(51) Int. Cl.
*A61N 1/18* (2006.01)

(52) U.S. Cl. .................. 607/48; 607/46; 607/49; 607/2
(58) Field of Classification Search ............... 607/43–51
See application file for complete search history.

(56) References Cited

U.S. PATENT DOCUMENTS

| 3,939,841 | A | 2/1976 | Dohring |
| 3,943,932 | A | 3/1976 | Woo |
| 4,398,545 | A | 8/1983 | Wilson |
| 4,512,351 | A | 4/1985 | Pohndorf |
| 5,397,338 | A | 3/1995 | Grey et al. |
| 5,449,378 | A | 9/1995 | Schouenborg |

(Continued)

FOREIGN PATENT DOCUMENTS

EP   0743533   11/1996

OTHER PUBLICATIONS

NeuroControl Corporation, NeuroControl StIM System brochure.

*Primary Examiner* — Niketa Patel
*Assistant Examiner* — Joseph Stoklosa
(74) *Attorney, Agent, or Firm* — Ryan Kromholz & Manion, S.C.

(57) ABSTRACT

Neurostimulation assemblies, systems, and methods make possible the providing of short-term therapy or diagnostic testing by providing electrical connections between muscles or nerves inside the body and stimulus generators or recording instruments mounted on the surface of the skin or carried outside the body. Neurostimulation assemblies, systems, and methods may include a carrier and a removable electronics pod, the electronics pod including stimulation generation circuitry, a power input bay to hold a disposable power source, and user interface components. The assemblies, systems, and methods are adapted to provide coordinated neurostimulation to multiple regions of the body.

9 Claims, 13 Drawing Sheets

U.S. PATENT DOCUMENTS

| | | |
|---|---|---|
| 5,607,461 A | 3/1997 | Lathrop |
| 5,721,482 A | 2/1998 | Benvegar et al. |
| 5,857,968 A | 1/1999 | Benja-Athon |
| 5,861,015 A | 1/1999 | Benja-Athon |
| 5,861,016 A | 1/1999 | Swing |
| 5,948,006 A * | 9/1999 | Mann ............................... 607/61 |
| 5,957,951 A | 9/1999 | Cazaux et al. |
| 6,016,449 A * | 1/2000 | Fischell et al. .................. 607/45 |
| 6,016,451 A | 1/2000 | Sanchez-Rodarte |
| 6,020,082 A | 2/2000 | Orlando |
| 6,026,328 A | 2/2000 | Peckham et al. |
| 6,072,299 A | 6/2000 | Kurle et al. |
| 6,108,579 A | 8/2000 | Snell et al. |
| 6,200,265 B1 | 3/2001 | Walsh et al. |
| 6,208,902 B1 * | 3/2001 | Boveja ............................. 607/46 |
| 6,257,906 B1 | 7/2001 | Price et al. |
| 6,275,737 B1 | 8/2001 | Mann |
| 6,338,347 B1 | 1/2002 | Chung |
| 6,366,809 B1 * | 4/2002 | Olson et al. ....................... 607/5 |
| 6,445,955 B1 | 9/2002 | Michelson et al. |
| 6,607,500 B2 | 8/2003 | Da Silva et al. |
| 6,622,037 B2 | 9/2003 | Kasano |
| 6,845,271 B2 | 1/2005 | Fang et al. |
| 6,904,324 B2 | 6/2005 | Bishay |
| 6,955,864 B1 | 10/2005 | Vaisnys et al. |
| 7,031,768 B2 | 4/2006 | Anderson et al. |
| 2002/0019652 A1 | 2/2002 | Da Silva et al. |
| 2002/0077572 A1 * | 6/2002 | Fang et al. ....................... 601/15 |
| 2003/0014088 A1 | 1/2003 | Fang et al. |
| 2003/0028170 A1 | 2/2003 | Anderson et al. |
| 2003/0032859 A1 | 2/2003 | Belson |
| 2003/0065368 A1 | 4/2003 | Van Der Hoeven |
| 2003/0074030 A1 | 4/2003 | Leyde et al. |
| 2003/0078633 A1 | 4/2003 | Firlik et al. |
| 2003/0120259 A1 | 6/2003 | Mickley |
| 2003/0195599 A1 | 10/2003 | Bishay |
| 2005/0182457 A1 | 8/2005 | Thrope et al. |
| 2005/0277844 A1 | 12/2005 | Strother et al. |
| 2006/0004421 A1 | 1/2006 | Bennett et al. |
| 2008/0097564 A1 | 4/2008 | Lathrop |

\* cited by examiner

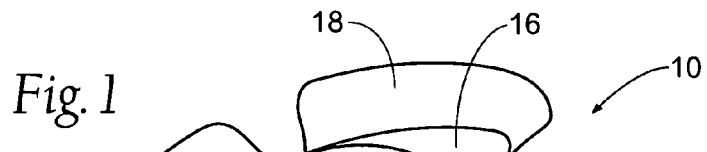
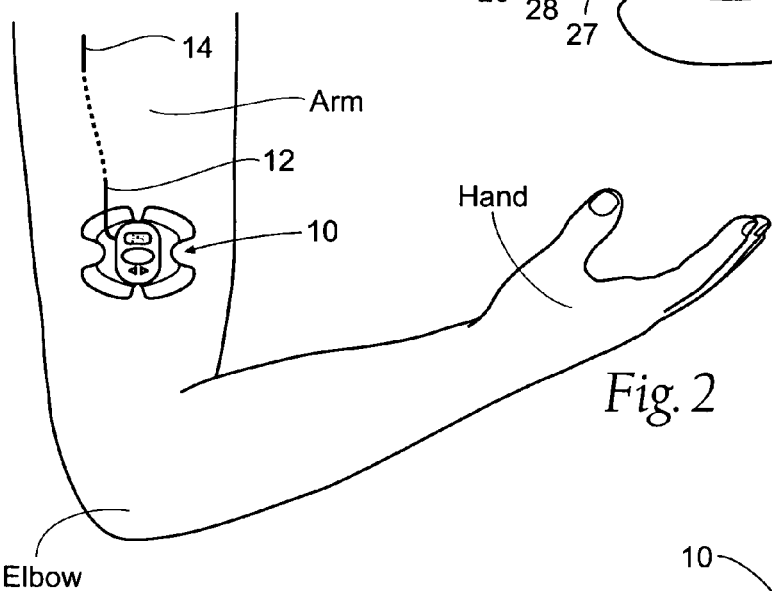
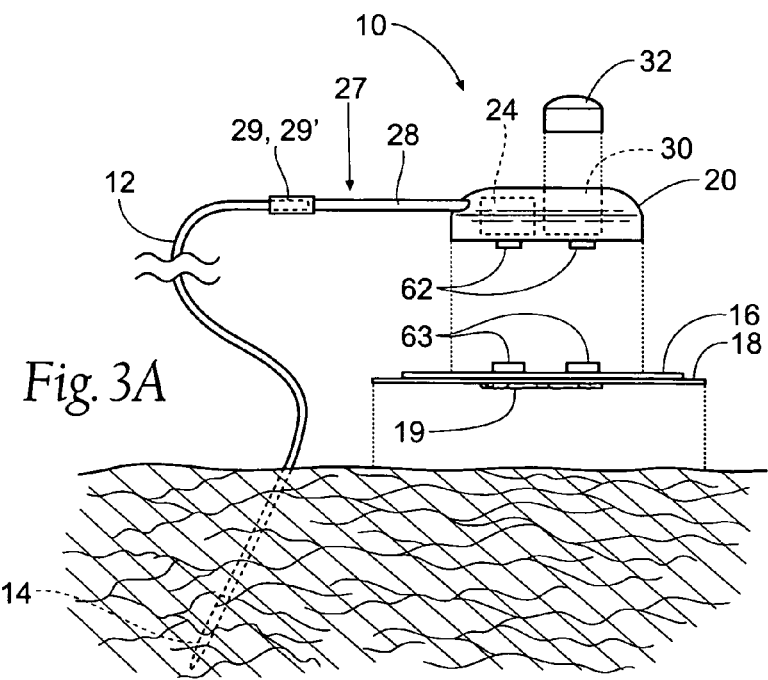

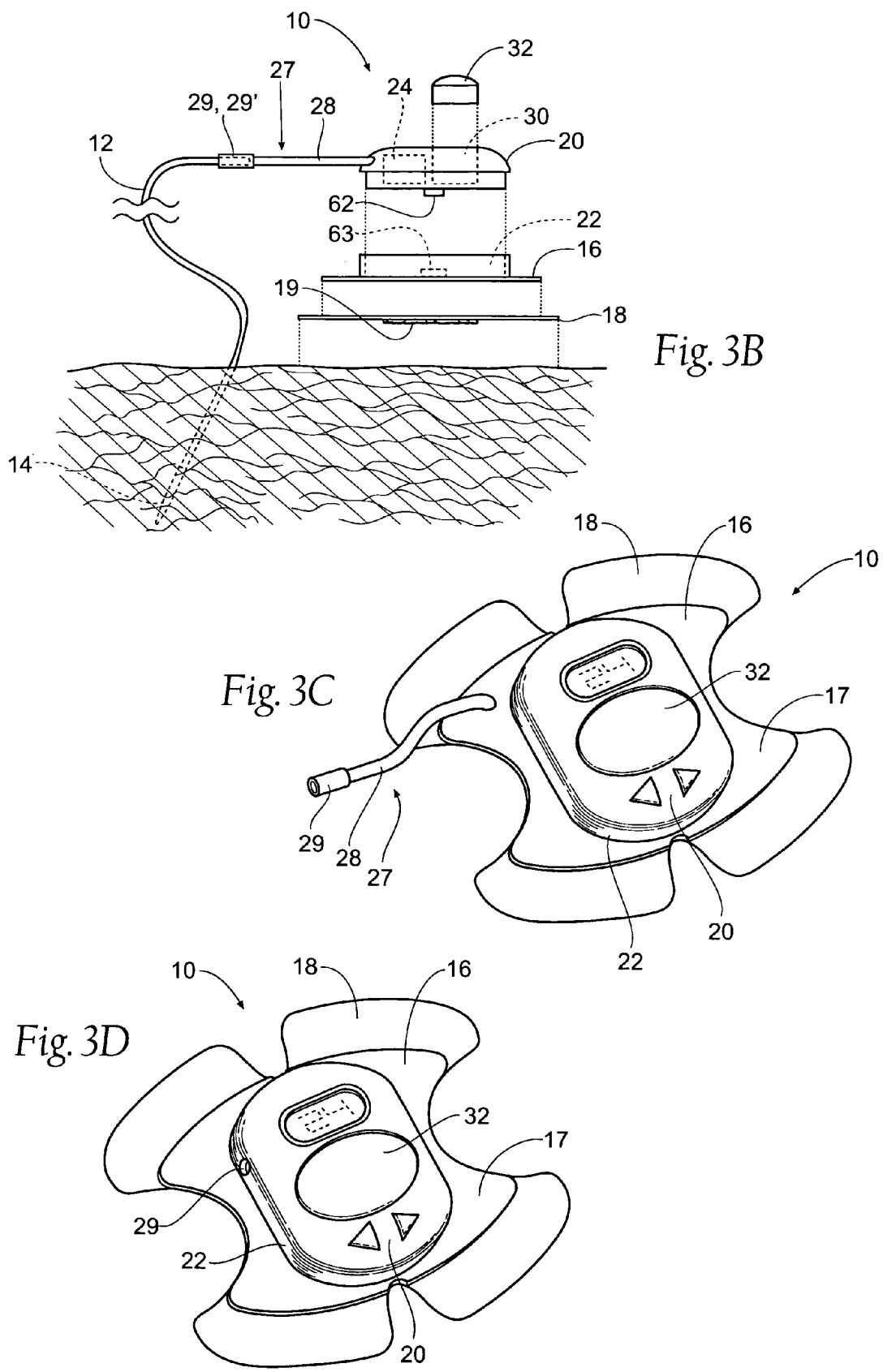

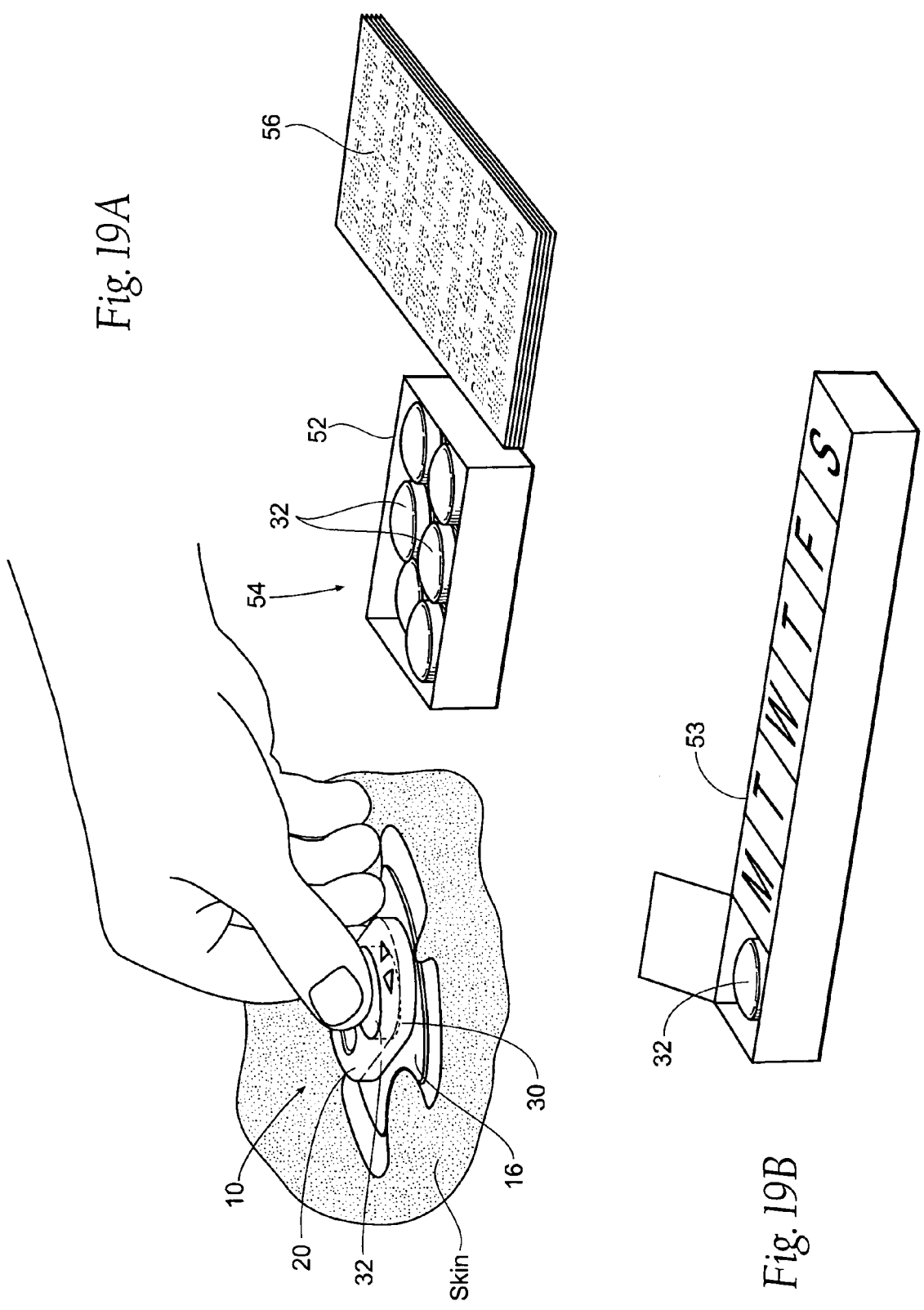

PORTABLE ASSEMBLIES, SYSTEMS, AND METHODS FOR PROVIDING FUNCTIONAL OR THERAPEUTIC NEUROSTIMULATION

RELATED APPLICATIONS

This application claims the benefit of U.S. Provisional Patent Application Ser. No. 60/801,315, filed May 18, 2006, and entitled "Portable Assemblies, Systems, and Methods for Providing Functional or Therapeutic Neuromuscular Stimulation," which is incorporated herein by reference.

This application is a continuation-in-part of U.S. patent application Ser. No. 11/056,591, filed Feb. 11, 2005 now U.S. Pat. No. 7,376,467, and entitled "Portable Assemblies, Systems and Methods for Providing Functional or Therapeutic Neuromuscular Stimulation," which claim the benefit of U.S. Provisional Patent Application Ser. No. 60/551,945, filed Mar. 10, 2004, and entitled "Steerable Introducer for a Percutaneous Electrode Usable in Association with Portable Percutaneous Assemblies, Systems and Methods for Providing Highly Selective Functional or Therapeutic Neurostimulation," which are incorporated herein by reference.

This application is also a continuation-in-part of U.S. patent application Ser. No. 10/777,771, now U.S. Pat. No. 7,120,499, filed Feb. 12, 2004, and entitled "Portable Percutaneous Assemblies, Systems and Methods for Providing Highly Selective Functional or Therapeutic Neurostimulation," which is incorporated herein by reference.

STATEMENT REGARDING FEDERALLY SPONSORED RESEARCH

This invention was made with government support under grant no. 1R43AR052211-01 awarded by the National Institutes of Health, through the National Institute of Arthritis and Musculoskeletal and Skin Diseases. The Government has certain rights in the invention.

FIELD OF INVENTION

This invention relates to assemblies, systems, and methods for providing neurostimulation to tissue.

BACKGROUND OF THE INVENTION

Neurostimulation, i.e., neuromuscular stimulation (the electrical excitation of nerves and/or muscle to directly elicit the contraction of muscles) and neuromodulation stimulation (the electrical excitation of nerves, often afferent nerves, to indirectly affect the stability or performance of a physiological system) and brain stimulation (the stimulation of cerebral or other central nervous system tissue) can provide functional and/or therapeutic outcomes. While existing systems and methods can provide remarkable benefits to individuals requiring neurostimulation, many quality of life issues still remain. For example, existing systems perform a single, dedicated stimulation function, and are unable to operate in a fashion to provide coordinated stimulation to multiple regions of a body. Furthermore, these controllers are, by today's standards, relatively large and awkward to manipulate and transport.

There exist both external and implantable devices for providing neurostimulation in diverse therapeutic and functional restorations indications. These neurostimulators are able to provide treatment therapy to individual portions of the body. The operation of these devices typically includes the use of an electrode placed either on the external surface of the skin, a vaginal or anal electrode, and/or a surgically implanted electrode. In the case of external neurostimulators, a percutaneous lead having an electrode is coupled to the external stimulator and the lead implanted within the body to deliver electrical stimulation to the select portion of the patient's body.

Existing systems commonly use line power or battery power to operate stimulation circuitry and to generate stimulation pulses. The power is generally not controllable, meaning that without appropriate user controls—that may or may not be used, the system could produce stimulation pulses as long as the system is connected to line power or the battery has enough capacity to operate the system, both of which could be for days, weeks, or even months.

When a battery is used for existing systems, the battery is incidental to the stimulation regime and is replaced at the end of its battery life. The battery is included to provide only a source of power, with the battery selection typically being a compromise between the physical size of the battery and as long of a battery life as possible, i.e., the battery is typically as small as possible but provides as long of a battery life as possible. While the existing systems and methods provide the capability of providing power and user controls, many limitations and issues still remain.

Systems and methods for providing coordinated stimulation to multiple areas of the body are not practical with known stimulators. Multiple individual stimulators may be used to provide stimulation to multiple areas of the body, but there lacks effective systems and methods that are able to coordinate the stimulation to multiple areas throughout the body.

It is time that systems and methods for providing neurostimulation address not only specific prosthetic or therapeutic objections, but also address the quality of life of the individual requiring neurostimulation, including the ability to control the power to the stimulation circuitry and to provide coordinated stimulation to multiple regions of a body.

SUMMARY OF THE INVENTION

The invention provides improved assemblies, systems, and methods for providing prosthetic or therapeutic neurostimulation.

One aspect of the invention provides portable, percutaneous or surface mounted neurostimulation assemblies, systems and methods that provide electrical connections between muscles or nerves inside the body and stimulus generators or recording instruments temporarily mounted on the surface of the skin or carried outside the body.

The assemblies, systems, and methods may, in use, be coupled by percutaneous leads to electrodes, which are implanted below the skin surface, or, alternatively, may be coupled to conventional surface mounted electrodes, and positioned at a targeted tissue region or regions. The neurostimulation assemblies, systems, and methods apply highly selective patterns of neurostimulation only to the targeted region or regions, to achieve one or more highly selective therapeutic and/or diagnostic outcomes. The patterns can vary according to desired therapeutic and/or diagnostic objectives. The indications can include, e.g., the highly selective treatment of pain or muscle dysfunction, and/or the highly selective promotion of healing of tissue or bone, and/or the highly selective diagnosis of the effectiveness of a prospective functional electrical stimulation treatment by a future, permanently implanted device. In addition, the controller interface from the user to the neurostimulation assemblies, systems, and methods may be wireless or may be manually entered via a user interface.

The neurostimulation assemblies, systems, and methods comprise a skin-worn patch or carrier. The carrier can be readily carried, e.g., by use of a pressure-sensitive adhesive, without discomfort and without affecting body image on, for example, an arm, a leg, or torso of an individual. In place of worn on the skin, the patch or carrier may also be carried by the patient, or secured to clothing, a bed, or to movable devices to allow for patient mobility.

The carrier carries a removable and replaceable electronics pod, which generates the desired electrical current patterns. The pod houses microprocessor-based, programmable circuitry that generates stimulus currents, time or sequence stimulation pulses, monitors system status, and logs and monitors usage. The electronics pod may be configured, if desired, to accept wireless RF based commands for both wireless programming and wireless patient control.

The electronics pod also includes an electrode connection region, to physically and electrically couple percutaneous electrode leads to the circuitry of the electronics pod or to the surface mounted electrodes.

The electronics pod further includes a power input bay, to receive a small, lightweight, disposable power source, which can be released and replaced as prescribed. The power source provides power to the electronics pod.

It is contemplated that, in a typical regime prescribed using the neurostimulation assemblies, systems, and methods, an individual will be instructed to regularly remove and discard the power source (e.g., about once a day, once a week, or as necessary), replacing it with a fresh power source. This arrangement simplifies meeting the power demands of the electronics pod and easily allows the prescription of therapies of differing duration (e.g., apply stimulation every eight hours, every day, or once a week). The use of the neurostimulation assemblies, systems, and methods thereby parallels a normal, accustomed medication regime, with the power source being replaced at a prescribed frequency similar to an individual administering a medication regime in pill form.

The power input bay can also serve as a communication interface. The communication interface may be plugged into a mating communications interface on an external device, or may have a wireless interface to an external device. Through this link, a caregiver or clinician can individually program the operation of a given electronics pod. If need be, the caregiver or clinician can modulate various stimulus parameters in real time.

The assemblies, systems, and methods make possible many different outcomes, e.g., (i) acute pain relief through treatment of pain or muscle dysfunction via the application of electrical stimulation to muscles (or their enervating nerves) with compromised volitional control due to injury to the peripheral or central nervous system (e.g., limb trauma, stroke, central nervous system diseases, etc.); and/or (ii) maintenance of muscle function and prevention of disuse atrophy through temporary stimulation to maintain muscle strength, mass, peripheral blood flow, etc., following a temporary disruption of function by disease or injury; and/or (iii) enhanced tissue and bone regeneration through the provision of small DC currents (or very low frequency AC currents) in bone or tissue to aid or speed healing of bone unions, tissue re-growth, etc; and/or (iv) treatment of pain or other conditions through the application of nerve stimulation to provide a neuro-modulation or inhibitory effect; and/or (v) post-surgical reconditioning to enhance muscle function and promote recovery of strength post-operatively; and/or (vi) anti-thrombosis therapy, e.g., by the stimulation of leg muscles to increase venous return of blood; and/or (vii) the treatment of osteoporosis by cyclic stimulation of muscles; and/or (viii) the short-term provision of electrical stimulation to evaluate the effectiveness of such treatment in advance of the implantation of a more permanent implant, for example, to evaluate whether a person having C5-6 tetraplegia has an innervated triceps muscle which could respond to treatment by electrical stimulation; and/or (ix) the short-term recording of biopotential signals generated in the body to aid in the diagnosis of medical conditions or in the assessment of the effectiveness of treatment methods; and/or (x) for functional benefits such as in the restoration of impaired or lost gait or upper extremity function.

Another aspect of the invention provides assemblies, systems, and methods for providing neurostimulation comprising at least one electrode, a carrier sized and configured to be worn by a user, an electronics pod removably carried on-board the carrier, the electronics pod including circuitry configured to generate a stimulation pulse to the electrode, and a power input bay carried on-board the electronics pod that is electrically coupled to the circuitry, the power input bay being sized and configured to accept a disposable power source.

The disposable power source includes circuitry, which may include non-volatile memory, to electronically store information about the power source. The electronics pod circuitry also may include non-volatile memory to electronically store information about the power source. The electronically stored information can comprise power source usage data (e.g., usage history), a unique power source identification, and power source capacity, for example.

The assemblies, systems, and methods may include a supply of power sources provided in an organizer that includes one or more disposable power sources for each day or period of the prescribed power source replacement regime. The organizer can take the form of a daily pill case that includes one or more compartments to hold one or more disposable power sources for each day or period of the prescribed power source replacement regime.

The electronics pod may also include a visual output, such as a display carried on-board the electronics pod. The visual output can also be provided by an illumination source that illuminates at least a portion of the electronics pod.

Other features and advantages of the inventions are set forth in the following specification and attached drawings.

BRIEF DESCRIPTION OF THE DRAWINGS

FIG. 1 is a perspective view of a neurostimulation assembly that provides electrical connections between muscles or nerves inside the body and stimulus generators temporarily mounted on the surface of the skin or carried outside the body.

FIG. 2 is a view of the neurostimulation assembly shown in FIG. 1 worn on a temporary basis on an external skin surface of an arm.

FIGS. 3A and 3B are exploded side views of alternative embodiments of the neurostimulation assembly shown in FIG. 1, showing its coupling to percutaneous leads to electrodes, which are implanted below the skin surface in a targeted tissue region or regions.

FIGS. 3C and 3D are perspective views of alternative embodiments of the neurostimulation assembly shown in FIG. 1, showing alternative configurations for coupling the neurostimulation assembly to percutaneous leads.

FIG. 19A is a perspective view of a neurostimulation system comprising a neurostimulation assembly of the type shown in FIG. 1 in association with a prescribed supply of replacement power sources and instructions for using the a neurostimulation assembly, including the powering of the neurostimulation therapy by inserting a fresh power source, just as an individual on a medication regime "doses" their medication therapy by taking a pill.

FIG. 19B is a perspective view of a power source pill case or organizer to aid in patient compliance of the prescribed neurostimulation regime.

Figure 4:
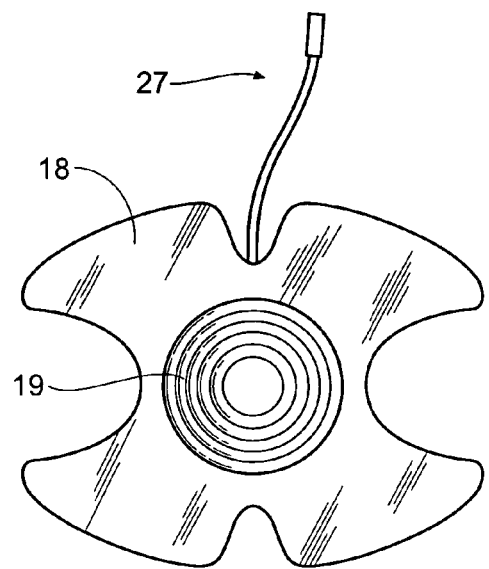
FIG. 4 is a bottom plan view of the neurostimulation assembly shown in FIG. 1, showing an adhesive region including a return electrode.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with providing neurostimulation for prosthetic or therapeutic purposes. That is because the features and advantages that arise due to the invention are well suited to this purpose. Still, it should be appreciated that the various aspects of the invention can be applied to achieve other objectives as well.

I. Neurostimulation Assembly Overview

FIG. 1 shows a neurostimulation assembly 10. As FIG. 2 shows, the neurostimulation assembly 10 is sized and configured so that, in use, it can be conveniently worn on a temporary basis. By "worn," it is meant that the assembly 10 may be removably skin mounted, or may also be carried by the patient (i.e., user), or secured to the patient's clothing, a bed, or to movable devices to allow for patient mobility. By "temporary," it is meant that the presence of the neurostimulation assembly 10 can be well tolerated without discomfort for a period of time from several hours to a month or two, after which the neurostimulation assembly 10 can be removed and discarded. During the period of use, the neurostimulation assembly 10 may be removed and reattached for hygiene maintenance. Desirably, the assembly 10 will be constructed in a manner to conform to at least the IPX1 standard for water ingress. The assembly 10 may be constructed in a manner to conform to higher standards as well, such as to allow the patient to wear the neurostimulation assembly 10 in the shower.

As FIGS. 3A and 3B show, the neurostimulation assembly 10 is, in use, releasably coupled to percutaneous leads 12 having electrodes 14, which are implanted below the skin surface in a targeted tissue region or regions. The tissue region or regions are targeted prior to implantation of the electrodes 14 due to their muscular and/or neural morphologies in light of desired therapeutic and/or functional and/or diagnostic objectives.

In use, the neurostimulation assembly 10 generates and distributes electrical current patterns through the percutaneous leads 12 to the electrodes 14 and back to a return electrode. In this way, the neurostimulation assembly 10 applies highly selective patterns of neurostimulation only to the targeted region or regions, to achieve one or more highly selective therapeutic and/or diagnostic outcomes. As will be described in greater detail later, the inputs/stimulation parameters can vary according to desired therapeutic and/or diagnostic objectives. For example, the outcomes can comprise the highly selective treatment of pain or muscle dysfunction, and/or the highly selective promotion of healing of tissue or bone, and/or the highly selective diagnosis of the effectiveness of a prospective functional electrical stimulation treatment.

II. Desirable Technical Features

The neurostimulation assembly 10 can incorporate various technical features to enhance its usability, which will now be described.

A. The Carrier

In its most basic form (see FIGS. 1, 3A, and 3B), the neurostimulation assembly 10 comprises a disposable patch or carrier 16. The carrier 16 desirably is sized and configured as a compact, lightweight, and flexible assembly made, e.g., of an inert, formed or machined plastic or metal material.

In a representative embodiment, the carrier 16 measures about two to four inches in diameter, weighing, e.g., about five grams, and may include a number of wings 17 to increase the mounting surface area. At this size, the carrier 16 can be readily worn without discomfort and in a cosmetically acceptable way (as FIG. 2 shows). The flexible carrier material and shape will allow the neurostimulation assembly 10 to be positioned on curved surfaces of the body, such as an arm, shoulder, leg, stomach, and back, for example.

B. The Adhesive Region

At least a portion of, and likely a larger surface area than the undersurface of the carrier 16 (see FIGS. 1, 3A, and 3B), includes a disposable adhesive region or patch 18. The adhesive region 18 may be an integral component of the carrier 16 (as shown in 3A), or a separate component (as shown in 3B). The function of the adhesive region 18 is to temporarily secure the carrier 16 to an external skin surface during use. For example, an inert, conventional pressure sensitive adhesive or tape can be used. Desirably, the dermal adhesive region contains a bacteriostatic sealant that prevents skin irritation or superficial infection, which could lead to premature removal.

The adhesive region 18 can also include an electrically conductive material. In this arrangement, the adhesive region 18 can serve as, or include, a surface return electrode 19, so that monopolar electrodes 14 can be implanted, if desired. The surface return electrode 19 is desired over a needle style return electrode because the surface electrode 19 reduces possible infection to the patient, does not require additional specialized surgery for installation, and the surface electrode provides a larger surface area than a needle electrode. The surface return electrode 19 may also have an adhesive character to help maintain the neurostimulation assembly 10 on the skin surface.

Figure 5:
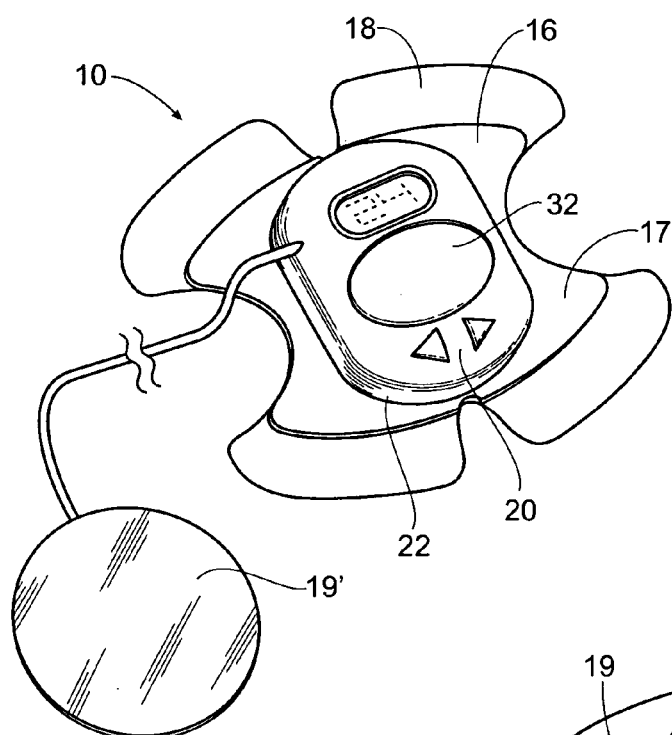
FIG. 5 is a perspective view of a neurostimulation assembly of the type shown in FIG. 1, showing a secondary return electrode connected to the stimulation assembly.
Figure 6:
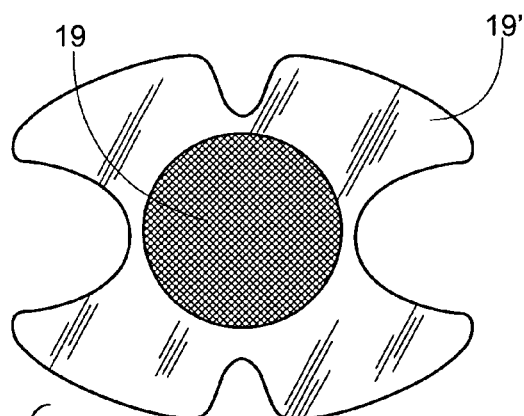
FIG. 6 is a bottom view of a neuromuscular stimulation system assembly of the type shown in FIG. 1, showing the adhesive region including both an active electrode portion and a return electrode portion.

When the adhesive region 18 including a surface return electrode 19 is an integral part of the carrier 16, or a separate component, the surface electrode is electrically coupled to the carrier to provide an electrical connection to an electronics pod 20 coupled to or carried in the carrier 16 (to be described below). In a representative embodiment, the return electrode 19 measures about one to three inches in diameter. This size range will present a surface area that is large enough that no sensory or motor stimulation would occur at the return electrode site. The return electrode 19 can also serve as an active electrode when it is used as a surface mounted stimulation system. In this configuration, a secondary return electrode 19' would be tethered to the stimulation system (see FIG. 5), or self contained within a concentric ring, such as the adhesive region 18 (see FIG. 6).

C. The Electronics Pod

The carrier 16 further carries an electronics pod 20, which generates the desired electrical current patterns and can communicate with an external programming system or controller 46.

As FIG. 3A shows, the electronics pod 20 can comprise a component or an assembly, such as a molded plastic component or assembly that can be removably coupled to the carrier 16. In an alternative embodiment, the electronics pod 20 may be inserted into and removed from an electronics bay 22 on the carrier 16 (see FIG. 3B). Having an electronics pod 20 that can be separated from the carrier 16 may be desired when the need to replace a carrier 16, or the electronics pod 20, during a course of treatment is necessary. For example, replacement of a carrier 16 without replacement of the electronics pod 20 may be desired if the anticipated length of use of the neurostimulation assembly 10 is going to be long enough to expect a degradation of adhesive properties of the adhesive region 18, or when the adhesive region 18 includes a return electrode 19 and may undergo, with use, degradation of adhesive properties and/or electrical conductivity. Alternatively, the electronics pod 20 can comprise an integral, non-removable part of the carrier 16.

Regardless of whether the electronics pod 20 is removable from the carrier 16 (see FIGS. 3A, 3B, and 10A) or not, the pod 20 houses microprocessor-based (microcontroller) circuitry 24 that generates stimulus waveforms, time or sequence stimulation pulses, logs and monitors usage, monitors system status, and can communicate directly to the clinician or indirectly through the use of an external programmer or controller. As a representative example, the stimulation desirably has a biphasic waveform (net DC current less than 10 microAmps), adjustable from about 0 mA to about 20 mA based on electrode type and the tissue type being stimulated, pulse durations adjustable from about 5 microseconds or less up to 500 microseconds or more, and a frequency of about 10 Hz to about 150 Hz. Most muscle stimulation applications will be in the 10 Hz to about 20 Hz region, and pain management may use the higher frequencies. The stimulus current (amplitude) may be user selectable and the pulse duration may be limited to clinician selectable.

The circuitry 24 desirably includes non-volatile memory, such as a flash memory device or an EEPROM memory chip to carry embedded, programmable code 26. The code 26 expresses the pre-programmed rules or algorithms under which the stimulation timing and command signals are generated. The circuitry 24 can be carried in a single location or at various locations on the pod 20, and may be fabricated on flexible or flex-rigid PC board using a very high density technique.

D. The Lead Connector

As FIGS. 1, 3A, and 3B show, the electronics pod 20 also includes one or more lead connectors 27. The function of the lead connector 27 is to physically and electrically couple the terminus of the percutaneous electrode leads 12 to the circuitry 24 of the electronics pod 20 (as FIGS. 3A and 3B show). When multiple connectors 27 are used, each lead connector 27 is able to distribute the electrical current patterns in channels, i.e., each electrode 14 comprises a channel, so that highly selective stimulation patterns can be applied through multiple electrodes 14. One or more channels may be provided.

The lead connector(s) 27 can be provided/constructed in various ways. In the illustrated embodiments, the lead connector 27 comprises a pig-tail cable 28 extending off the electronics pod 20 and ending with a connector 29. It is to be appreciated that the pig-tail cable could extend off the carrier 16 as well (see FIG. 3C). It is also to be appreciated that the connector 29 could be integral with the electronics pod 20 or carrier 16 as well, i.e., without the pig-tail cable 28. Such an integral connector may mate with an insulated lead 12 that does not include a mating connector 29' (as described below). The integral connector 29 on the electronics pod 20 or carrier 16 would terminate and electrically connect to the insulated lead 12 (see FIG. 3D).

FIG. 3A shows each connector 29 being sized and configured to slidably receive a mating connector 29' coupled to a lead 12 or a secondary return electrode 19'. Both connectors 29 and 29' may be touch proof connectors to help maintain a consistent and reliable electrical connection. Each lead connector 27 may be labeled with a number or other indicia to record the channel of the electronics circuitry 24 that is coupled to each channel.

Alternative embodiments are possible. Coupling the electrode leads 12 to the electronics pod 20 or carrier 16, can be accomplished by a locking motion, a button, or a lever arm, or an Allen drive that is pushed, or slid, or pulled, or twisted, for example.

Desirably, (see FIG. 3A), the electronics pod 20 can be removed and replaced with a snap-fit of the electronics pod 20 off of or on to the carrier 16. Alternatively, the electronics pod 20 can be removed and replaced with a snap-fit of the electronics pod 20 out of or into the electronics bay 22 of the carrier 16 (see FIG. 3B). An electrical connection region or contact(s) 62 on the pod 20 electrically couples to a mating connection region or contact(s) 63 on the carrier 16, or alternatively in the electronics bay 22, to couple the circuitry 24 on the pod 20 to the return electrode 19 positioned on the underside of or integral with the carrier 16. A single set of mating connection region or contacts 62, 63 may be used (as shown in FIG. 3B, or more than one set of mating connection region or contacts 62, 63 may be used (as shown in FIG. 3A). More than one set may help to eliminate any rotational movement between the carrier 16 and the electronics pod 20.

E. The Power Input/Communication Bay

Referring back to FIGS. 3A and 3B, the electronics pod 20 further includes a power input bay 30. One function of the power input bay 30 is to releasably receive an interchangeable, and (desirably) disposable power source 32. The power source 32 provides power to the electronics pod 20. The power source 32 may incorporate a snap-fit mechanism to secure the power source into the power input bay 30.

It is contemplated that, in a typical regime prescribed using the neurostimulation assembly 10, an individual will be instructed to remove and discard the power source 32 about once a day, replacing it with a fresh power source 32. This arrangement simplifies meeting the power demands of the electronics pod 20 while easily allowing the prescription of therapies of differing duration (e.g., remove and replace the power source every other day or once a week to provide the stimulation on a prescribed, intermittent basis). The use of the neurostimulation assembly 10 will thereby parallel a normal, accustomed medication regime, with the power source 32 being replaced in the same frequency an individual administers medication in pill form. The power source 32 may be provided in an over-molded housing 34 to ease attachment and removal.

Figure 7:
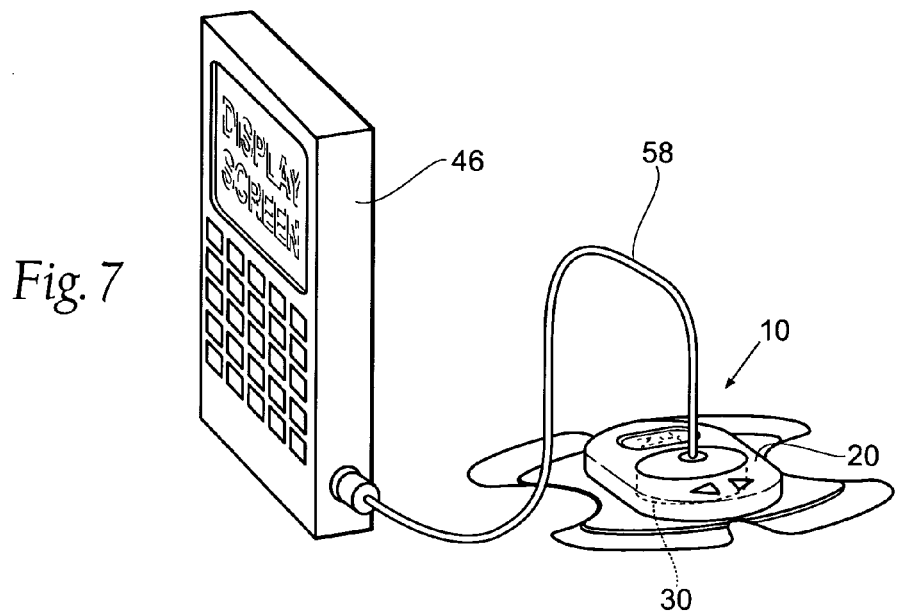
FIG. 7 is a perspective view of a neurostimulation assembly of the type shown in FIG. 1 coupled to an external programming instrument.

The power input bay 30 can also serve as a communication interface. As FIG. 7 shows, when free of a power source 32, the bay 30 can be used to plug in a cable 58 to an external programming device 46 or computer. This will also be described later. This makes possible linking of the electronics pod 20 to an external programming device 46 or computer. Through this link, information and programming input can be exchanged and data can be downloaded from the electronics pod 20.

In this way, the neurostimulation assembly 10 makes it possible for a care giver or clinician to individually program the operation of a given electronics pod 20 to the extent permitted by the embedded, programmable code 26. It should be appreciated, of course, that instead of using a cable interface, as shown, a wireless link 59 (e.g., RF magnetically coupled, infrared, or RF) could be used to place the electronics pod 20 in communication with an external programming device 46 or computer (see FIG. 8).

F. The Power Source

Figure 9:
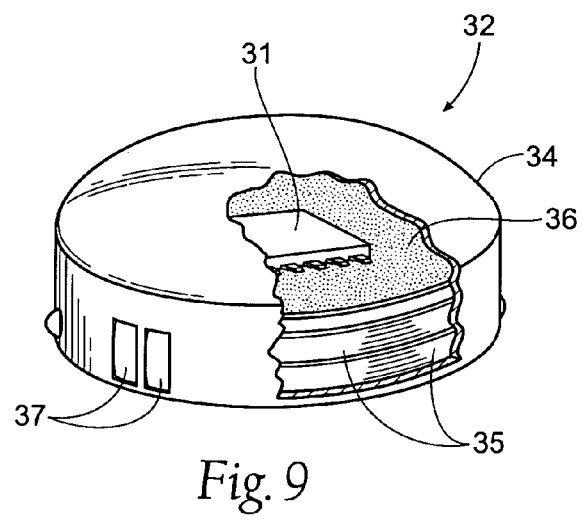
FIG. 9 is a perspective view with a partial cutaway showing the power source housing and internal and external components.

The disposable power source 32 can be described as a self-contained, limited life power source. The disposable power source 32 may comprise a housing 34 including one or more batteries 35, e.g., an alkaline, lithium, or Silver Oxide battery, circuitry 36, and contacts 37 to provide the power to the electronics pod 20 (see FIG. 9).

The circuitry 36 of the disposable power source 32 may be used to electronically store information about the power source. The circuitry 36 may include a non-volatile memory 31 to store the power source information. The capacity of the power source 32 may be stored, e.g., the power source may identify itself as a one hour power source or a six hour power source or a twenty-four hour power source. The circuitry 36 may also identify each unit (e.g., to provide a unique identification, such as serial number), and/or electronically identify the total power usage (service time) provided to date by the power source.

The replacement of the power source 32 is the method by which the patient initiates another session of use or episode of treatment. Sessions/episodes of usage/treatment may be interrupted by removing the power source 32, and re-inserting the same power source will resume stimulation; but the total duration of stimulation from that one power source 32 is still limited to the value defined for that power source, e.g., eight hours of use, or twelve hours, or twenty-four hours. The battery(s) 35 and electrical components 36 will be inaccessible to battery replacement. The battery or batteries 35 are secured within the housing 34, such as a molded plastic housing, to aid in handling of the power source. The housing also prevents the use of a power source not intended for the neurostimulation assembly 10. The housing may include multiple pieces and may be made inaccessible by sonic welding, gluing, or other permanent fastening methods, to secure the housing together. Even if the battery 35 was replaced, the circuitry 36 of the power source 32 would prevent its reuse.

Instructions for use 56 are intended to be furnished by a clinician or caregiver or physician prescribing the release and replacement of the disposable power source 32 according to a prescribed power source replacement regime. The prescribed power source replacement regime includes the replacement of the disposable power source 32 on a prescribed repeated basis similar to administering a "pill" under a prescribed pill-based medication regime.

A supply of disposable power sources 32 for administration according to the prescribed power source replacement regime, i.e., a usage or therapy regime, is intended to be provided, each power source thereby providing a "dose" of power for the circuitry to provide the delivery of the neurostimulation. With the prescribed power source replacement regime (as with a prescribed pill-based medication regime), a caregiver/clinician/physician instructs the patient to remove and replace the disposable power source 32 on a repeated or periodic basis (like taking a dose of medication in pill form) to administer to the circuitry a dose of power so the circuitry can generate a dose of neurostimulation. In this way, the prescribed power sources replacement regime has the effect or flavor of a prescribed pill-based medication regime, and not an end-of-life battery timeout.

G. The User Interface

Figure 10A:
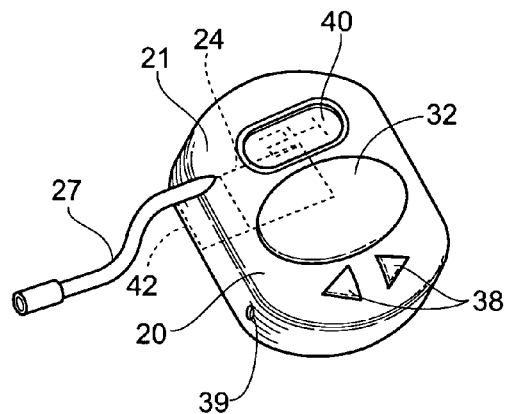
FIG. 10A is a perspective view of the electronics pod shown in FIG. 1, showing components of the electronics pod, including user interface components.
Figure 10B:
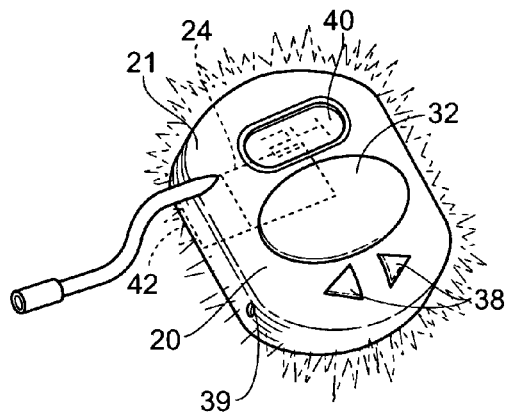
FIG. 10B is a perspective view of the electronics pod shown in FIG. 10A, showing the glowing or illumination feature.

The electronics pod 20 as shown in FIGS. 10A and 10B desirably includes one or more features that provide an interface mechanism for the patient and/or the clinician. The interface feature allows for the input and output of neurostimulation assembly information, such as stimulus regime parameters and system status, and the interface may be manual, audio, or visual, or a combination. For example, the electronics pod 20 may include control means 38, e.g., two button controls 38 to allow the patient to control stimulation amplitude setting or some other stimulus intensity adjustment. The electronics pod 20 may also include one or more recessed buttons 39, e.g., a paper clip access switch, to provide control for the clinician to access clinician controllable settings, such as the stimulus pulse duration and/or stimulus frequency, for example.

The particular setting level can be displayed using a display 40, e.g., an LCD or LED display, to visually identify to the patient the setting level, and to allow the patient to record the setting within a therapy diary, which could then be presented to a physician for review. The operating modes and stimulus parameters may be entered manually using the control means 38 and/or 39, and easily interpreted via the visual output or feedback display 40. In one embodiment, the setting level is a combination of pulse duration and amplitude, the specifics of which are unknown to the patient. The display 40 may also provide a data read-out function for the clinician. For example, the display 40 may provide information such as the total duration of stimulus provided, the average or median stimulus level selected by the patient, and perhaps the total number of power sources used.

The display 40 may also provide status information, such as power source status or system status. For power source status, the stimulation assembly 10 may indicate the power source 32 positioned within the power input bay 30 has limited power remaining, or that the power source has provided its maximum amount of power. For system status, the stimulation assembly 10 may indicate the electronics pod 20 is not properly connected to the carrier 16 (or positioned within the electronics bay 22), or the electrical connections to the lead 12 or return electrode 19 are not working, for example.

In addition to or in place of the visual feedback display 40, visual output or feedback may also be provided by an illuminating electronics pod 20, or portions of the electronics pod, such as the pod cover 21. The pod cover 21 may comprise a material, e.g., a semi-transparent material, able to allow an illumination source 42, such as one or more LEDs, to create a "glowing" or "illuminated" appearance, as shown in FIG. 10B. The illumination source 42 would be coupled to the circuitry 24 within the electronics pod 20. Status information can be visually provided to the user by using various blinking or pulsing configurations, illumination brightness, changing colors, or any combination, for example. As with the display 40, status information may include power source status and system status.

III. Representative Neurostimulation Assembly Circuitry

Figure 11:
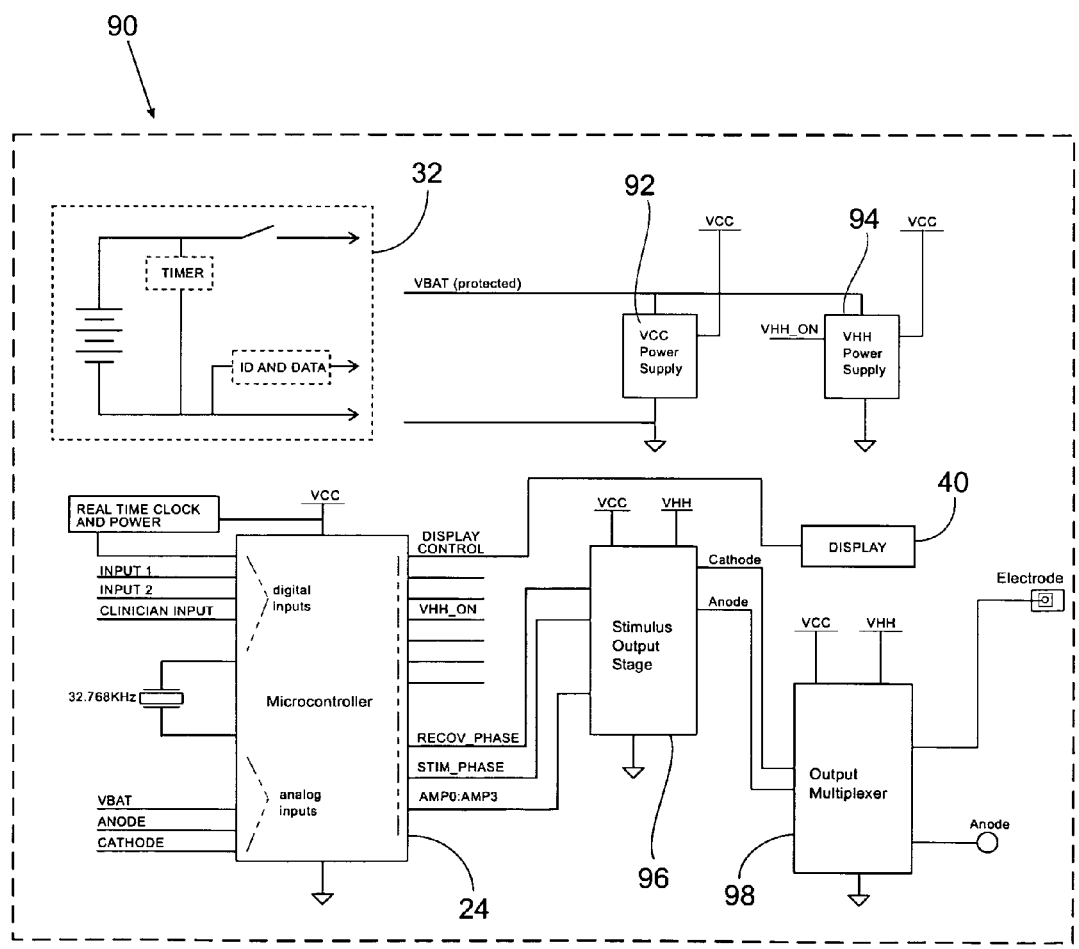
FIG. 11 is a block diagram of a circuit that the neurostimulation assembly shown in FIG. 1 may utilize.

FIG. 11 shows an embodiment of a block diagram circuit 90 for the neurostimulation assembly 10 that takes into account the desirable technical features of the neurostimulation assembly design discussed above. The circuit 90 can be grouped into functional blocks, which generally correspond to the association and interconnection of the electronic components.

In FIG. 11, six functional blocks are shown: (A) the Microprocessor Circuitry 24; (B) the Power Source 32; (C) the VCC Power Supply 92; (D) the VHH Power Supply 94; (E) the Stimulus Output Stage(s) 96; and (F) the Output Multiplexer 98.

For each of these blocks, the associated functions, and possible key components and circuit description are now described.

A. The Microcontroller Circuitry

The microcontroller circuitry 24 may be responsible for the following functions:

(1) The timing and sequencing of most of the electronics pod 20 functions including the generation of stimulus pulses and the quantification of usage by the power source, (2) A/D converter to measure output pulse, power source voltage, and VHH voltage, (3) D/A converter may set the pulse amplitude, (4) Control for display 40 and/or illumination source 42, (5) And alternatively, control for a real time clock; the real time clock to provide a time signal to the microprocessor circuitry from the first powering of the electronics pod 20, and keep time without the presence of the power source 32 for about 21 days.

The use of microcontroller based circuitry incorporating flash programmable memory allows the operating software of the neurostimulator as well as the stimulus parameters and settings to be stored in non-volatile memory (data remains safely stored even when the power source 32 becomes fully discharged or is removed). The non-volatile memory is also used to store usage history information. The VCC power supply 92 must support the power requirements of the microcontroller circuitry 24 during any flash memory erase and program operations.

Although the microcontroller circuit 24 may be a single component, the firmware is developed as a number of separate modules that deal with specific needs and hardware peripherals. The functions and routines of these software modules are executed sequentially; but the execution of these modules are timed and coordinated so as to effectively function simultaneously. The microcontroller operations that are associated directly with a given hardware functional block are described with that block.

The Components of the Microcontroller Circuit may include:

(1) A single chip microcontroller 25. This component may be a member of the Texas Instruments MSP430 family of flash programmable, micro-power, highly integrated mixed signal microcontroller. Likely family members to be used include the MSP430F1610, MSP430F1611, MSP430F1612, MSP430F168, and the MSP430F169. Each of these parts has numerous internal peripherals, and a micropower internal organization that allows unused peripherals to be configured by minimal power dissipation, and an instruction set that supports bursts of operation separated by intervals of sleep where the microcontroller suspends most functions.

(2) A miniature, quartz crystal for establishing precise timing of the microcontroller. This may be a 32.768 KHz quartz crystal.

(3) Miscellaneous power decoupling and analog signal filtering capacitors.

B. The Power Source

The Power Source 32 (including associated microcontroller circuitry 24 actions) may be responsible for the following functions:

(1) monitor the battery voltage, (2) suspend stimulation when the power source 32 voltage becomes very low, (3) discontinue stimulation when the power source has been used for a predetermined amount of time, e.g., 24 hours, or whatever time is prescribed by the clinician, within a margin, (4) prevent (with single fault tolerance) the delivery of excessive current from the power source 32, and (5) provide power to the rest of the circuitry of the neurostimulation assembly, e.g., VCC and VHH power supplies.

In one embodiment, power management controls are generally included with the electronics pod 20. As previously described, the circuitry 24 contains non-volatile memory, which is adapted to store power source usage information written by and read by the electronic pod 20.

(1) The electronics pod 20 and associated microcontroller circuitry 24 would communicate with the power source 32 and periodically update usage data, such as the length of time, or the total number of pulses for which that the power source has been used. The circuitry 24 would also be adapted to read and write power source usage data to the non-volatile memory 31 in the power source 32. The electronics pod 20 would then stop the generation and application of stimulation after the power source 32 has been used for its prescribed time or should the power source fail prematurely.

(2) Each power source may also be uniquely identified, such as by including information in non-volatile memory 31.

In an alternative embodiment, power management controls are included with the power source 32 and requires minimal support from the electronics pod 20.

(1) The power source is isolated from all circuitry via a MOSFET switch that requires active closure by the circuitry on the power source.

(2) The power source circuitry would include a resettable polymer based fuse, where the voltage drop across the fuse is read by the power source circuitry as an indicator of current draw.

(3) A low cost microcontroller could be included to keep track of the time the power source has been providing power.

C. The VCC Power Supply

The VCC Power Supply 92 is generally responsible for the following functions:

(1) Provide the microcontroller circuitry 24 and other circuitry with a regulated DC voltage typically about 1.0 VDC to about 3.3 VDC despite changes in the power source voltage.

The VCC power supply may include a micropower, low drop out, linear voltage regulator; e.g., Microchip NCP1700T-3302, Maxim Semiconductor MAX1725, or Texas Instruments TPS79730. The VCC power supply may also include a charge pump or switched mode power supply regulator such as Texas Instrument TPS60124 or Maxim MAX679.

D. VHH Power Supply

The VHH power supply 94 is generally responsible for the following functions:

(1) Provide the stimulus output stage 96 and multiplexer 98, if used, with a programmable DC voltage high enough to drive the required cathodic phase current through the electrode circuit plus the voltage drops across the stimulator stage, and possibly an output coupling capacitor. VHH is typically about 12 VDC to about 35 VDC.

The Components of the VHH Power Supply might include:

(1) Micropower, inductor based (fly-back topology) switch mode power supply; e.g., Texas Instruments TPS61045, Texas Instruments TPS61041, Linear Technology LT1615, or Linear Technology LT3459.

(2) The microcontroller circuit 24 monitors VHH for detection of a VHH power supply failure, system failures, and optimizing VHH for the exhibited electrode circuit impedance.

E. Stimulus Output Stage

Figure 12:
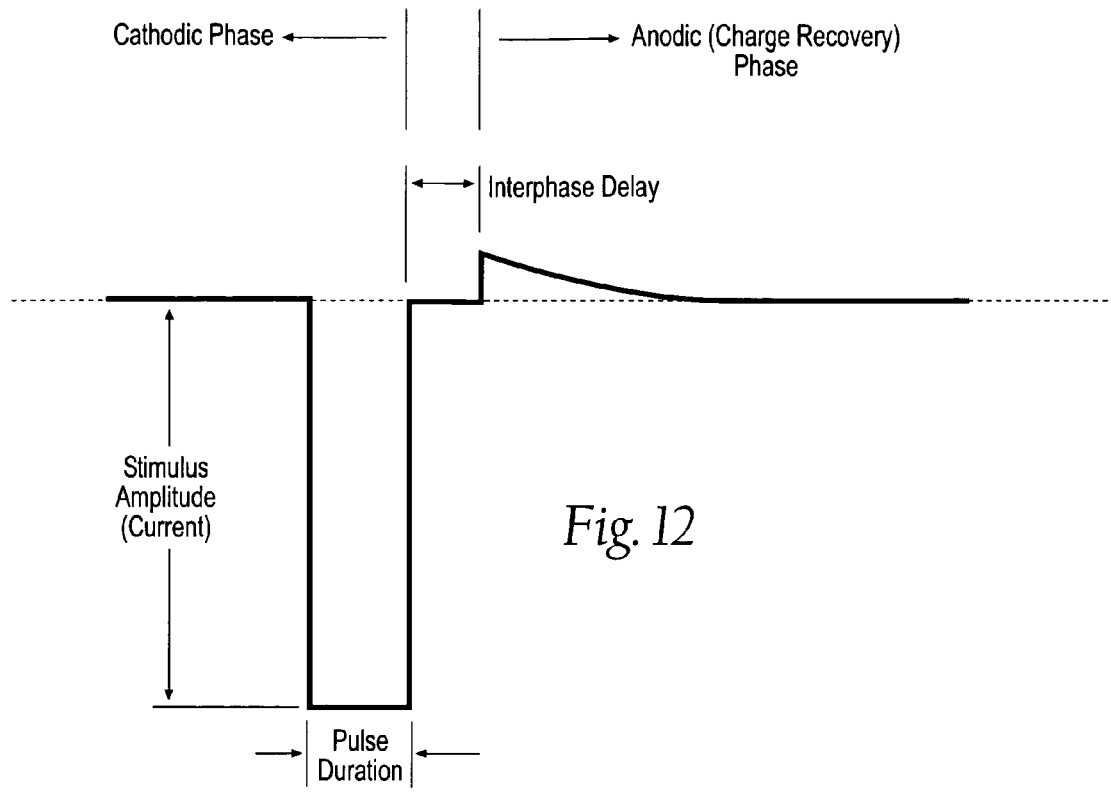
FIG. 12 is a graphical view of a desirable biphasic stimulus pulse output of the neurostimulation assembly for use with the system shown in FIG. 1.

The Stimulus Output Stage(s) 96 is generally responsible for the following functions:

(1) Generate the identified biphasic stimulus current with selected cathodic phase amplitude, pulse width, and frequency. The recovery phase may incorporate a maximum current limit; and there may be a delay time (most likely a fixed delay) between the cathodic phase and the recovery phase (see FIG. 12). Typical currents (cathodic phase) vary from about 0.5 mA to about 20 mA based on the electrode construction and the nature of the tissue being stimulated. Electrode circuit impedances can vary with the electrode and the application, but are likely to be less than 2,000 ohms and greater than 100 ohms across a range of electrode types.

Two alternative configurations of the stimulus output stage will be described. In the first configuration:

(1) The cathodic phase current through the electrode circuit is established by a high gain (HFE) NPN transistor with emitter degeneration shunted by four switched shunting resistors (switched lines AMP0-AMP3) to form a controlled current sink.

(2) The microcontroller circuit 24 monitors the cathode voltage to confirm the correct operation of the output coupling capacitor, to detect system failures, and to optimize VHH for the exhibited electrode circuit impedance; i.e., to measure the electrode circuit impedance.

In a second alternative configuration:

(1) A low-threshold N-channel MOSFET driven by an op-amp with fast enable/disable functions to provide a low quiescent current current sink.

(2) A precision voltage reference of about 2.048 v for both the microcontroller circuit external reference and the current sink reference.

(3) Four switched shunting resistors (switched lines AMP0-AMP3) to form the controlled current sink.

(4) The microcontroller circuit 24 monitors the cathode voltage to confirm the correct operation of the output coupling capacitor, to detect system failures, and to optimize VHH for the exhibited electrode circuit impedance; i.e., to measure the electrode circuit impedance.

In either configuration, the switched resistors could be replaced by a DAC, if available as an on-chip peripheral at the microcontroller. In either configuration, the start and ending of the cathodic phase current is timed by the microcontroller.

F. The Output Multiplexer

The output multiplexer 98 is required only if more than one electrode circuit is required. The output multiplexer is responsible for routing the anode and cathode connections of the Stimulus Output Stage 96 to the appropriate electrode, i.e., electrode 14, return electrode 19, or both.

A representative output multiplexer configuration includes:

(1) A low ON resistance, micropower, dual 4×1 analog multiplexer; e.g. Maxim MAX4052, MAX384, Vishay DG412HS, or Pericom PS4066 or PS323 (with separate decoding logic or additional microcontroller address lines), and (2) Microcontroller circuitry 24 selects the electrode connections to carry the stimulus current (and time the interphase delay) via address lines.

IV. The Electrodes and Their Implantation

Figure 13:
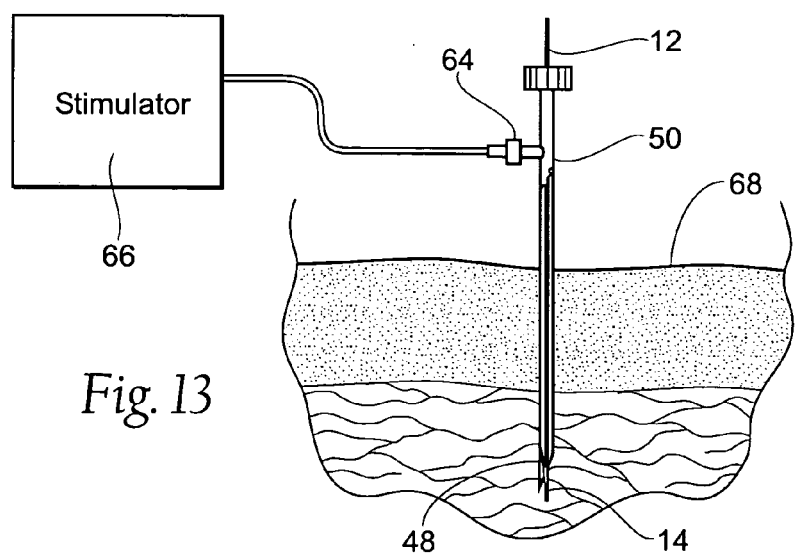
FIGS. 13 to 15 show the use of an electrode introducer to percutaneously implant an electrode in a targeted tissue region and for connection to a neurostimulation assembly as shown in FIG. 1.

The configuration of the electrodes 14 and the manner in which they are implanted can vary. A representative embodiment will be described, with reference to FIGS. 13 to 15.

In the illustrated embodiment, each electrode 14 and lead 12 comprises a thin, flexible component made of a metal and/or polymer material. By "thin," it is contemplated that the electrode 14 should not be greater than about 0.75 mm (0.030 inch) in diameter.

The electrode 14 and lead 12 can comprise, e.g., one or more coiled metal wires with in an open or flexible elastomer core. The wire can be insulated, e.g., with a biocompatible polymer film, such as polyfluorocarbon, polyimide, or parylene. The electrode 14 and lead 12 are desirably coated with a textured, bacteriostatic material, which helps to stabilize the electrode in a way that still permits easy removal at a later date and increases tolerance.

The electrode 14 and lead 12 are electrically insulated everywhere except at one (monopolar), or two (bipolar), or three (tripolar) conduction locations near its distal tip. Each of the conduction locations is connected to a conductor that runs the length of the electrode and lead, proving electrical continuity from the conduction location through the connectors 29 and 29' to the electronics pod 20. The conduction location may comprise a de-insulated area of an otherwise insulated conductor that runs the length of an-entirely insulated electrode. The de-insulated conduction region of the conductor can be formed differently, e.g., it can be wound with a different pitch, or wound with a larger or smaller diameter, or molded to a different dimension. The conduction location of the electrode may comprise a separate material (e.g., metal or a conductive polymer) exposed to the body tissue to which the conductor of the wire is bonded.

In an alternative configuration, the lead 12 does not terminate in a connector; rather an insulated lead is electrically connected to the electronics pod 20 or carrier 16 through an automated connection method that connects and terminates the lead 12.

The electrode 14 and lead 12 desirably possess mechanical properties in terms of flexibility and fatigue life that provide an operating life free of mechanical and/or electrical failure, taking into account the dynamics of the surrounding tissue (i.e., stretching, bending, pushing, pulling, crushing, etc.). The material of the electrode desirably discourages the in-growth of connective tissue along its length, so as not to inhibit its withdrawal at the end of its use. However, it may be desirable to encourage the in-growth of connective tissue at the distal tip of the electrode, to enhance its anchoring in tissue.

Figure 14:
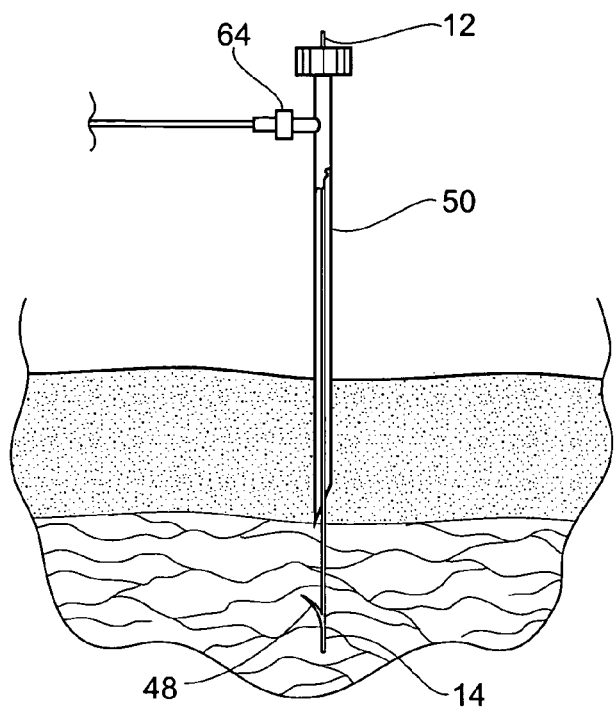
Figure 15:
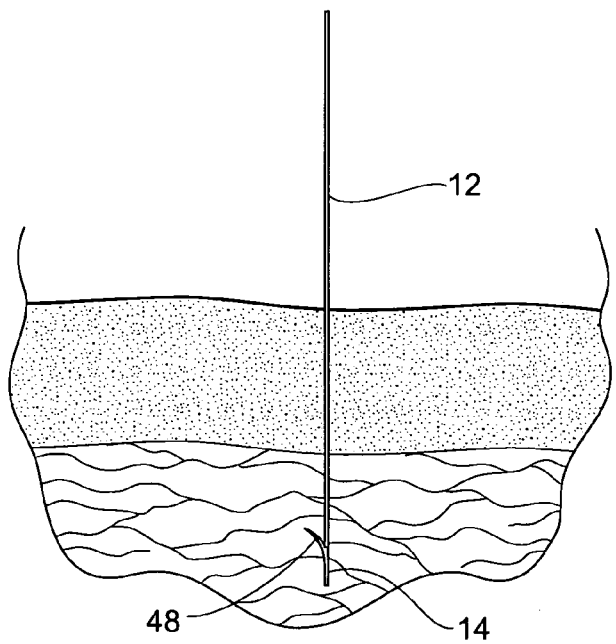
Figure 16:
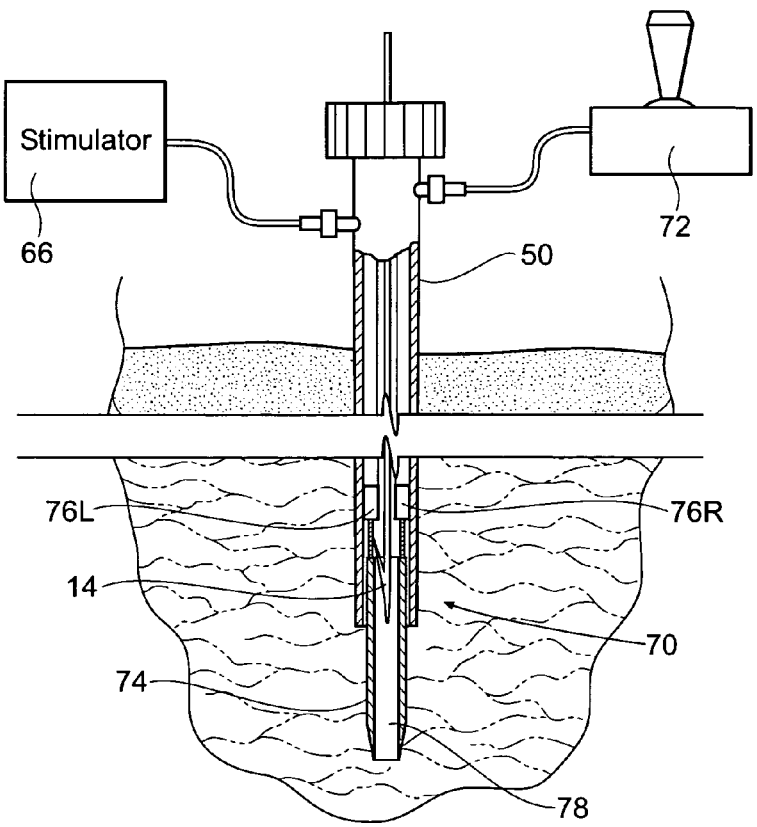
FIGS. 16 to 18 show an electrode introducer having a remotely deflectable, distal needle region to percutaneously steer an electrode into a desired implant location prior to connection to a neurostimulation assembly as shown in FIG. 1.

Furthermore, the desired electrode 14 may also include, at its distal tip, an anchoring element 48 (see FIGS. 14 and 15). In the illustrated embodiment, the anchoring element 48 takes the form of a simple barb. The anchoring element 48 is sized and configured so that, when in contact with tissue, it takes purchase in tissue, to resist dislodgement or migration of the electrode out of the correct location in the surrounding tissue. Desirably, the anchoring element 48 is prevented from fully engaging body tissue until after the electrode has been deployed. The electrode is not deployed until after it has been correctly located during the implantation (installation) process, as will be described in greater detail later.

In one embodiment, the electrode 14 and lead 12 can include a metal stylet within its core. Movement of the stylet with respect to the body of the electrode and/or an associated introducer (if used) is used to deploy the electrode by exposing the anchoring element 48 to body tissue. In this arrangement, the stylet is removed once the electrode 14 is located in the desired region.

In the illustrated embodiment (see FIGS. 13 and 14), an electrode 14 is percutaneously implanted housed within electrode introducer 50. The electrode introducer 50 comprises a shaft having sharpened needle-like distal tip, which penetrates skin and tissue leading to the targeted tissue region. The electrode 14 and lead 12 are loaded within a lumen in the introducer 50, with the anchoring element 48 shielded from full tissue contact within the shaft of the introducer 50 (see FIG. 13). In this way, the introducer can be freely manipulated in tissue in search of a desired final electrode implantation site (see FIG. 13) before deploying the electrode (see FIG. 14) and withdrawing the introducer 50 (see FIG. 15).

The electrode introducer 50 is insulated along the length of the shaft, except for those areas that correspond with the exposed conduction surfaces of the electrode 14 housed inside the introducer 50. These surfaces on the outside of the introducer 50 are electrically isolated from each other and from the shaft of the introducer 50. These surfaces are electrically connected to a connector 64 at the end of the introducer body (see FIGS. 13 and 14). This allows connection to a stimulating circuit 66 (see FIG. 13) during the implantation process. Applying stimulating current through the outside surfaces of the introducer 50 provides a close approximation to the response that the electrode 14 will provide when it is deployed at the current location of the introducer 50.

The electrode introducer 50 is sized and configured to be bent by hand prior to its insertion through the skin. This will allow the physician to place an electrode 14 in a location that is not in an unobstructed straight line with the insertion site. The construction and materials of the electrode introducer 50 allow bending without interfering with the deployment of the electrode 14 and withdrawal of the electrode introducer 50, leaving the electrode 14 in the tissue.

In an alternative embodiment (see FIGS. 16 to 18A, 17B, and 17C), the electrode introducer 50 includes a distal needle region 70 that can be deflected or steered by operation of a remote steering actuator 72. Remote bending of the needle region 70 is another way to facilitate guidance of the electrode 14 to a location that is not in an unobstructed straight line with the insertion site.

The creation of the bendable needle region 70 that can be remotely deflected can accomplished in various ways. In the illustrated embodiment, the needle region 70 comprises a semi-flexible, electrically conductive, needle extension 74. The needle extension 74 is telescopically fitted within the distal end of the introducer 50, meaning that the extension 74 is capable of sliding within the introducer 50. The semi-flexible needle extension 74 includes an interior lumen 78, which communicates with the interior lumen of the introducer 50, through which the electrode 14 passes. Thus, the electrode 14 can be passed through the lumen 78 of the needle extension 74 for deployment.

Small linear motors 76L and 76R, e.g., employing conventional micro-electromechanical system (MEMS) technology, couple the proximal ends of the needle extension 74 to the introducer 50. The motors 76L and 76R are desirably attached in a spaced apart relationship, which in the illustrated embodiment, is about 180-degrees.

Figure 17:
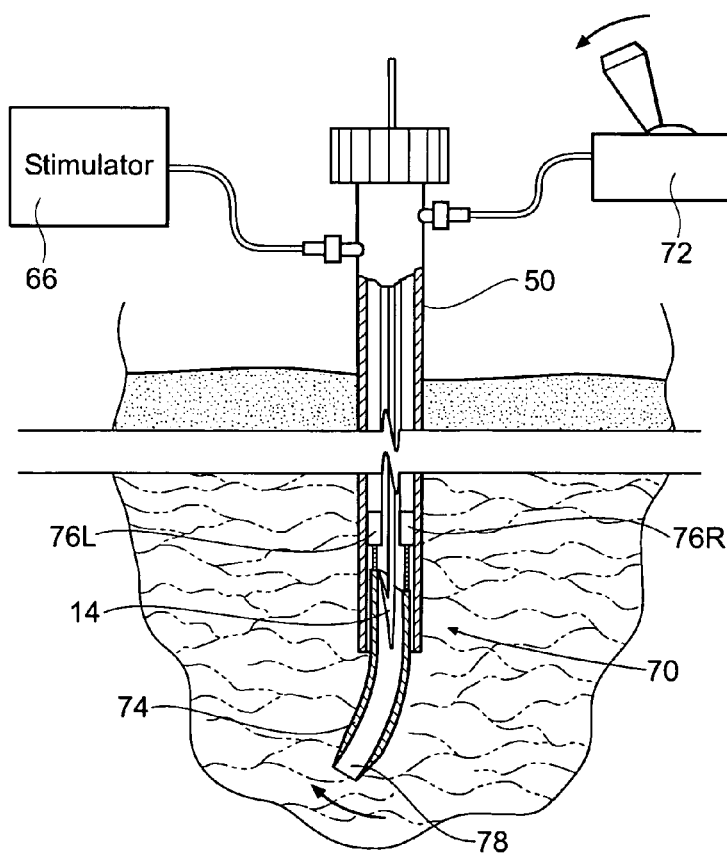
Figure 18:
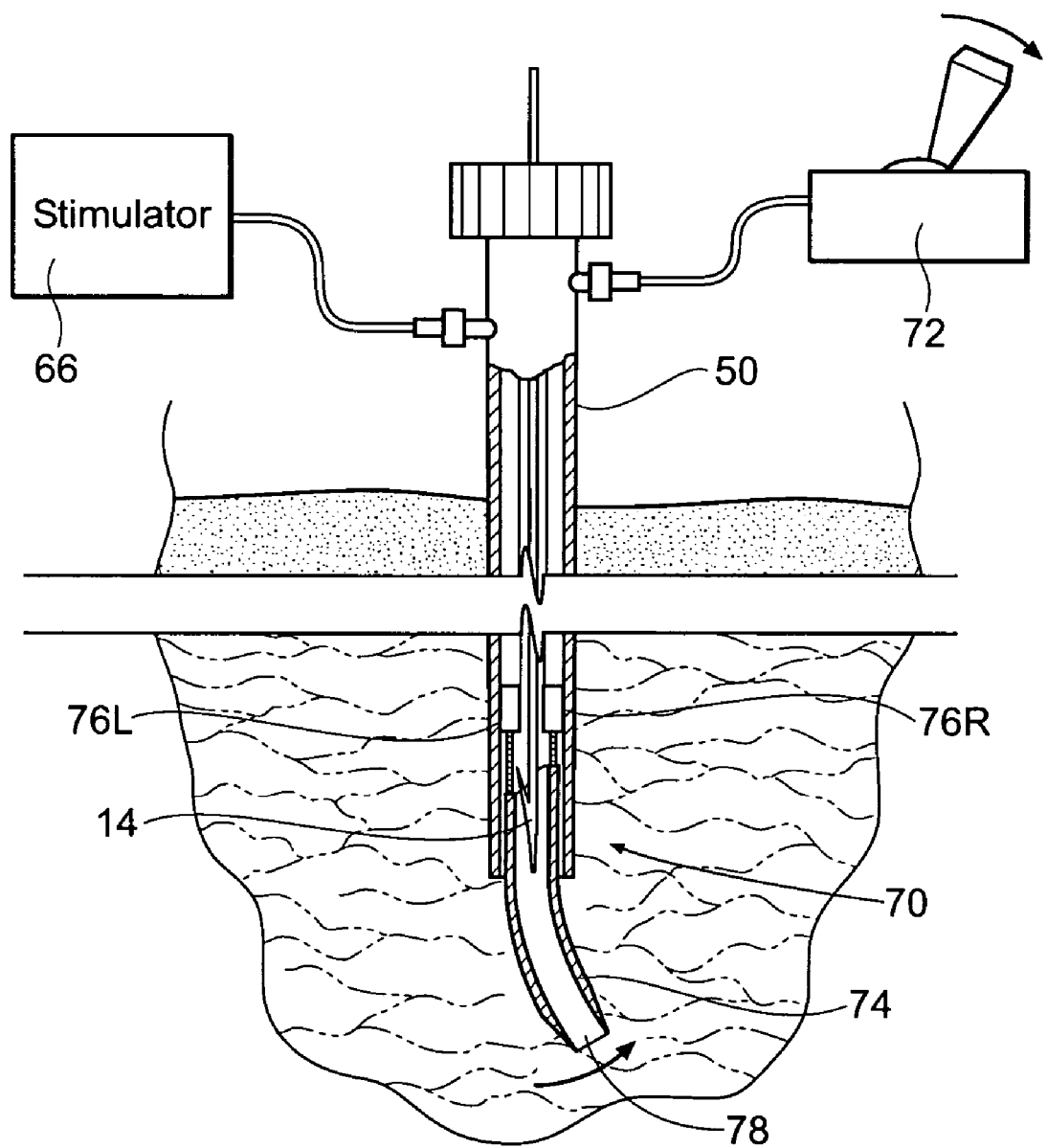

Driving the motors 76L and 76R at the same rate, forward or reverse, respectively extends or retracts the flexible extension 74 from the introducer 50 in a linear path. Driving the motors 76L and 76R at different rates, or in different directions, or both, imparts a bending torque on the needle extension 74, causing it to deflect. For example, driving the left side motor 76L at a faster forward rate than the right side motor 76R (or driving the left side motor 76L forward while driving the right side motor 76R in reverse) deflects the needle extension 74 to the right, as FIG. 18 shows. Conversely, driving the left side motor 76L at a slower rate than the right side motor 76R (or driving the right side motor 76R forward while driving the left side motor 76L in reverse) deflects the needle extension 74 to the left, as FIG. 17 shows.

In this arrangement, the steering actuator 72 can comprise, e.g., a conventional joystick device. By manipulating the joystick device 72, as FIGS. 17 and 18 show, variable drive rates/directions can be applied to the motors 76L and 76R, to deflect or steer the needle extension 74 in the desired direction. The path that the introducer 50 takes through tissue can thereby be directed. While guiding the introducer 50 in this fashion, stimulating current can be applied through the outside surfaces of the needle extension 74 until the location having the desired stimulation response is found. The electrode 14 can be deployed through the needle extension 74, fully engaging the electrode anchoring element 48 in body tissue, in the manner previously described, followed by a withdrawal of the introducer 50.

Instead of MEMS linear motors 76L and 76R, conventional push-pull steering wires could be passed through lumens in the introducer 50 and coupled to the needle extension 74. Manipulation of the actuator 72 pushes or pulls on the wires to affect bending of the extension 74 in the manner just described.

V. Installation of the Neurostimulation Assembly

Prior to installation, a clinician identifies a particular muscle and/or neural region to which a prescribed therapy using the neurostimulation assembly 10 will be applied. The particular types of therapy that are possible using the neurostimulation assembly 10 will be described later. Once the particular muscle and/or tissue region or regions are identified, the clinician proceeds to percutaneously implant one or more electrodes 14 and leads 12, one by one, through the desired skin region 68. While each lead 12 is implanted, the electrode introducer 50 applies a stimulation signal until a desired response is achieved, at which time the electrode 14 is deployed and the introducer 50 is withdrawn.

Upon implanting each electrode (see FIG. 13, for example), the clinician is able to route each electrode lead 12 to a lead connector 29 on the electronics pod 20 (or carrier 16).

The following illustration will describe the use of a neurostimulator assembly 10 that will be worn on the patient's exterior skin surface. It is to be appreciated that the neurostimulator assembly 10 could be carried by the patient or temporarily secured to a bed or other structure and the lead(s) 12 extend to the assembly 10. The carrier 16 is placed on the skin in a desirable region that allows electrical connectivity to the lead 12 and associated connector 29' (see FIGS. 2 and 3A). The carrier 16 is secured in place with the pressure sensitive adhesive 18 on the bottom of the carrier. As previously stated, the adhesive region desirably contains a bacteriostatic sealant that prevents skin irritation or superficial infection, which could lead to premature removal.

After implanting one or more electrodes 14 and routing each lead 12 to the carrier 16 the clinician may now snap fit the electronics pod 20 into carrier 16 (or into the electronics bay 22, if included). In addition, a power source 32 would also be snap-fit into the power input bay 30 in the electronics pod 20 to provide the power to the circuitry 24, as FIG. 3A shows. The clinician would be able to couple the connectors 29 and 29' together to complete the stimulation path. The neurostimulation assembly 10 is ready for use. It is to be appreciated that the electronics pod 20 and the power source 32 could be coupled to the carrier 16 when the carrier is secured to the skin.

Typically, as shown in FIG. 19A, a container 52 holding a prescribed number of replacement power sources 32, e.g., seven or fourteen, will be provided with the neurostimulation assembly 10, forming a neurostimulation system 54. The power source 32 can be likened to a "pill," the pill being a "dose" of power for the stimulation circuitry as a medicine pill provides a dose of medication for a prescribed pill-based medication regime. This gives the patient the responsibility of ownership in treatment, which boosts compliance during the treatment period and allows delivery of scheduled stimulation; e.g., every day or other day or once every week. The container 52 may also be in the form of a seven day (or more or less) pill case or similar organizer 53 that includes one or more compartments to hold one or more disposable power sources, or "pills," for each day or prescription period to aid in compliance (see FIG. 19B).

Instructions for use 56 may accompany the neurostimulation system 54. The instructions 56 prescribe use of the neurostimulation assembly 10, including the periodic removal and replacement of the power source 32 with a fresh power source 32. Thus, the instructions 56 prescribe a neurostimulation regime that includes a periodic "powering" or dosing, via power source replacement, of the neurostimulation assembly 10 in the same fashion that pill-based medication regime directs periodic "dosing" of the medication by taking of a pill. In the context of the neurostimulation system 54, a power source 32 becomes the therapeutic equivalent of a pill (i.e., it is part of a user action taken to extend treatment).

Figure 19C:
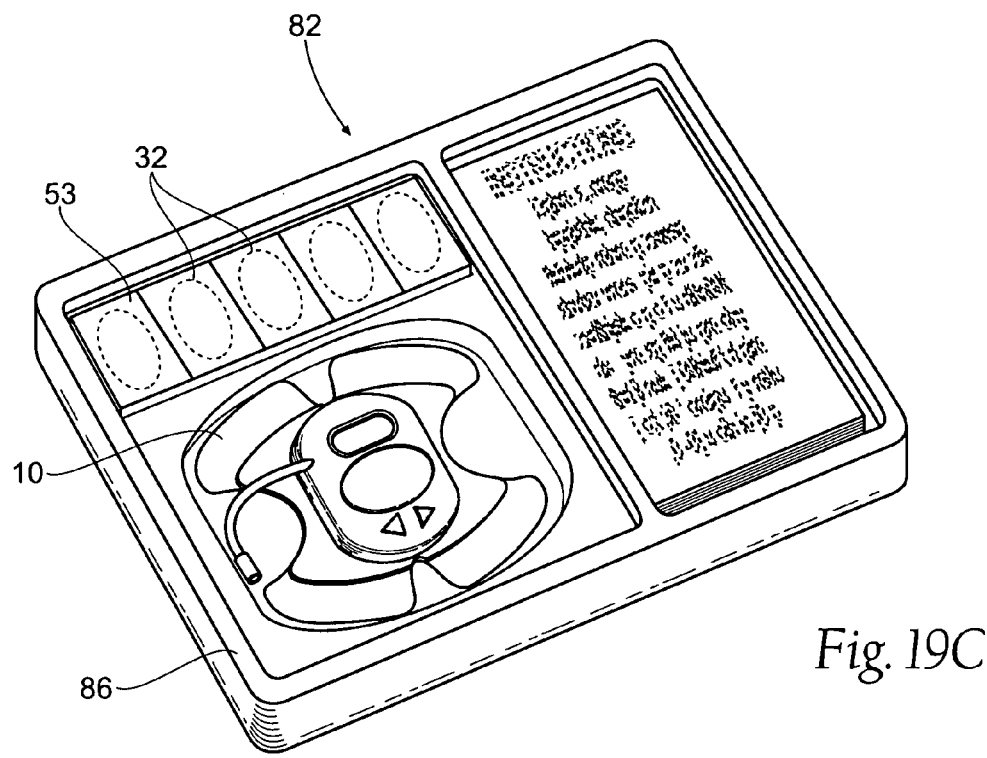
FIG. 19C is a plan view of a kit packaging the neurostimulation assembly and the pill case, along with instructions for use, as shown in FIGS. 19A and 19B.
Figure 19D:
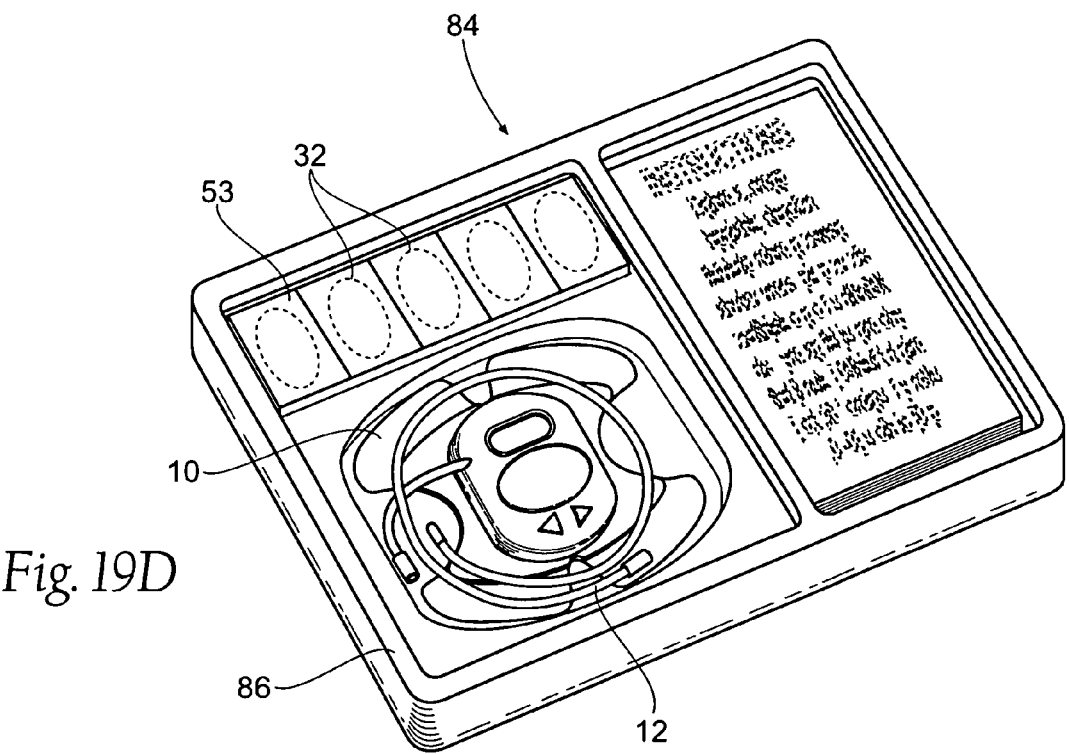
FIG. 19D is a plan view of an alternative kit similar to that shown in FIG. 19C, the alternative kit packaging the neurostimulation assembly, one or more leads, and the pill case, along with instructions for use.

As FIGS. 19C and 19D show, the various devices and components just described can be consolidated for use in functional kits 82 and 84. The kits can take various forms. In the illustrated embodiments, each kit 82, 84 comprises a sterile, wrapped assembly. Each kit 82, 84 includes an interior tray 86 made, e.g., from die cut cardboard, plastic sheet, or thermo-formed plastic material, which hold the contents. Each kit 82, 84 also desirably includes instructions for use 56 for using the contents of the kit to carry out a desired therapeutic and/or diagnostic objectives.

The instructions 56 can, of course vary. The instructions 56 shall be physically present in the kits, but can also be supplied separately. The instructions 56 can be embodied in separate instruction manuals, or in video or audio tapes, CD's, and DVD's. The instructions 56 for use can also be available through an internet web page.

The arrangement and contents of the kits 82, 84 can vary. For example, FIG. 19C shows a kit 82 containing the neurostimulation assembly 10 along with a pill container 52 or organizer 53 (as shown). The instructions for use 56 in the kit instruct the user in the removal and replacement of the neurostimulation assembly 10, along with the operation of the neurostimulation system 54. Kit 84 is similar to kit 82, except kit 84 also includes one or more leads 12. The instructions for use 56 in the kit 84 would also direct a clinician to place the neurostimulation assembly 10, implant the lead 12 and electrode 14, and couple the lead to the assembly 10, in addition to instructions for the user in the removal and replacement of the neurostimulation assembly 10, along with the operation of the neurostimulation system 54.

Figure 8:
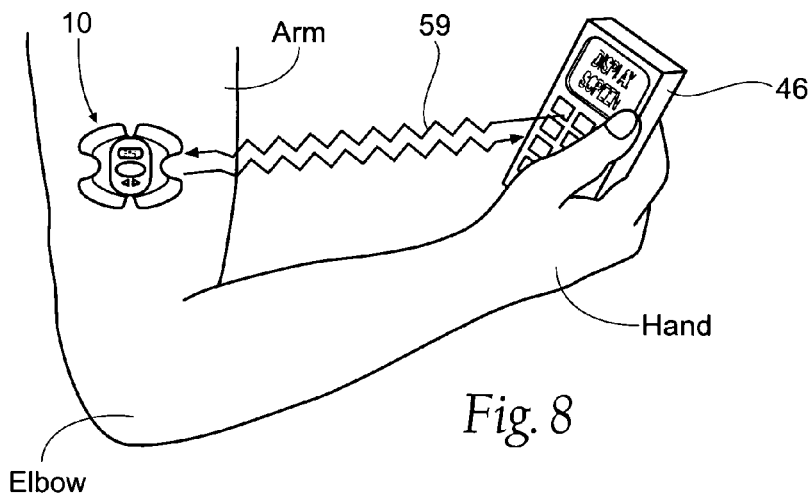
FIG. 8 is a perspective view of a neurostimulation assembly of the type shown in FIG. 1 in association with an external programming and control instrument that relies upon a wireless communication link.

As FIGS. 7 and 8 show, external desktop or handheld (desirably also battery powered) preprogrammed instruments 46 can be used to program stimulus regimes and parameters into the neurostimulation assembly 10, or to download recorded data from the neurostimulation assembly 10 for display and further processing. The instruments 46 can communicate with the neurostimulation assembly 10, e.g., by a cable connection 58, by radio frequency magnetic field coupling, by infrared, or by RF wireless 59. As before described, the power input bay 30 can additionally comprise a communications interface that is coupled to a communications cable 58 connected to the instrument 46. The communications cable 58 provides power to the neurostimulation assembly 10 during programming, as well as communications with the circuitry 24 of the neurostimulation assembly 10. The external programming instrument 46 can also be a general purpose personal computer or personal digital device fitted with a suitable custom program and a suitable cable or interface box for connection to the communications cable 58.

The programming instruments 46 allow a clinician to customize the stimulus parameters and regime timing residing in an individual neurostimulation assembly 10 according the specific needs of the user and the treatment goals of the clinician. The neurostimulation assembly 10 can, once customized, be disconnected from the programming system, allowing portable, or skin worn operation, as already described. The programming instruments also allow the retrieval of usage information allowing the clinician to accurately assess patient compliance with the prescribed treatment course or regime. Alternatively, and as previously described, the clinician may use the push buttons, display, and any recessed buttons to program the stimulus parameters and timing and to retrieve key usage data.

VI. Representative Use of the Neurostimulation Assembly/System

A. Overview

The neurostimulation assembly 10 and/or neurostimulation system 54, as described, make possible the providing of short-term therapy or diagnostic testing by providing electrical connections between muscles or nerves inside the body and stimulus generators or recording instruments mounted on the surface of the skin or carried outside the body. The programmable code 26 of the neurostimulation assembly 10 and/or neurostimulation system 54 can be programmed to perform a host of neurostimulation functions, representative examples of which will be described for the purpose of illustration.

B. Temporary, Non-Surgical Diagnostic Assessment

Prior to the administering of a specific permanent implanted neuromodulation or neurostimulation system, (e.g. urinary incontinence, vagal nerve stimulation for epilepsy treatment, spinal cord stimulators for pain reduction), the neurostimulation assembly 10 and/or neurostimulation system 54 can be applied to provide the physician and their patient with some assurance that through the temporary stimulation of the end organ, the treatment is viable. This would allow the physician to screen patients that may not be candidates for the permanent treatment, or otherwise, may not find the effect of the treatment to be worth the effort of the surgical implantation of a permanent system.

A specific example involves the treatment of C5-6 tetraplegics. C5-6 tetraplegics are unable to extend their elbow. Without elbow extension, they are limited to accessing only the area directly in front of their body, requiring assistance in many of their activities of daily living. They rely on the use of their biceps muscle to perform most of their upper extremity tasks. With limited or no hand function they rely on adaptive equipment to accomplish many self care activities such as grooming and hygiene as well as feeding.

An existing surgical procedure to restore elbow extension is to transfer a portion of the deltoid muscle into the triceps. This non-reversible surgical process requires extensive surgical intervention, prolonged post-operative immobilization and extended rehabilitation. Additionally, the timeframe to achieve a useful result post-operatively once the person recuperates from the surgery is no less than three months and may take up to a year to achieve full elbow extension.

As an alternative to the Deltoid to Triceps transfer, a pulse generator can be implanted in a minimal invasive way in association with a lead/electrode in electrical conductive contact with peripheral motor nerves that innervate the triceps muscle. The pulse generator can be programmed to provide single channel electrical stimulation to peripheral motor nerves that innervate the triceps muscle to produce elbow extension. Adding the ability to extend the elbow can significantly increase reach and work space thus allowing greater independence. With elbow extension, the ability to reach overhead or extend the arm outward to the side greatly increases this work space thereby allowing much more freedom to complete tasks otherwise out of their reach. This ability to extent also provides better control of objects as it provides co-contraction of the elbow flexors and extensors simultaneously.

A first phase of treatment or evaluation period is desirably conducted to identify whether a person has an innervated triceps muscle which responds to electrical stimulation. If the muscle is innervated and functioning, the physician will identify if stimulation to this muscle can provide adequate elbow extension both in a horizontal plane such as reaching out and in a vertical plane for reaching up. The individual must also be able to overcome the force of this triceps stimulation with their biceps muscle by demonstrating that they can still flex their elbow during stimulation of the triceps. Usually this can be tested by asking the person to bring their hand to their mouth.

The evaluation process can be accomplished with a percutaneous or surface neurostimulation device of the type described herein. The stimulation device carries the on-board electronics pod 20, which generates the desired electrical current patterns to cause electrical stimulation of radial nerve innervation to the triceps. The pod houses microprocessor-based, programmable circuitry 24 that generates stimulus currents, time or sequence stimulation pulses, and logs and monitors usage. As before described, a user interface/programmer may be used.

If percutaneous electrodes are used, the circuitry of the electronics pod 20 is physically and electrically coupled to the percutaneous leads of the electrodes. After placement of the percutaneous leads, the stimulator settings can be programmed, either by direct coupling or a wireless link to a programmer. Stimulation will be applied using 0-200 μsec pulses at 20 Hz. The force of triceps activation can be determined by the strength of their biceps muscle. The subject must maintain the ability to comfortably flex their elbow during triceps stimulation. A stronger biceps will allow for stronger stimulation to the triceps. The subject may require a conditioning phase of one to two weeks to build up the endurance of the triceps muscle following the initial set up. The subject must demonstrate the ability to flex the elbow while stimulation to the triceps is provided. Thus relaxation of biceps will allow elbow extension.

The individual will be scheduled for a second phase of treatment if electrical stimulation of the radial nerve innervation to the triceps using the surface or percutaneous stimulation program provides active elbow extension expanding the individual's previous work space.

The second phase of treatment includes the replacement of the first phase stimulation devices with the implantation of an implantable pulse generator and associated lead/electrode.

C. Coordinated Muscle Stimulation

Muscle weakness has been found to occur after only short periods of inactivity. As a result, peripheral muscle strength training for in-bed bound patients, such as those in an intensive care unit, has been used in an attempt to maintain some muscle conditioning, and at a minimum to slow muscle strength degradation.

Figure 20:
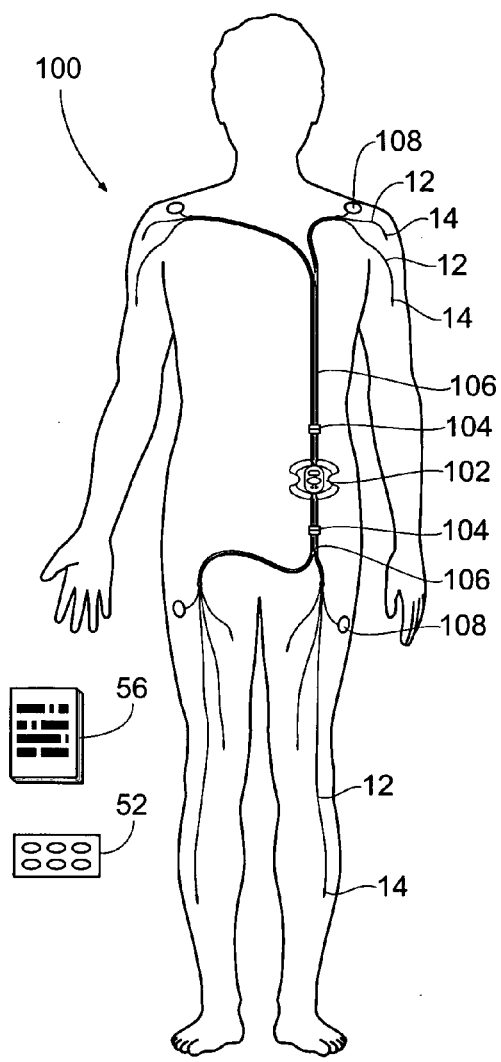
FIG. 20 is an anatomical view showing an alternative configuration of a neurostimulation assembly and system, the system including a harnessed multi-channel stimulation assembly capable of providing coordinated neurostimulation to multiple regions of the body.
Figure 21:
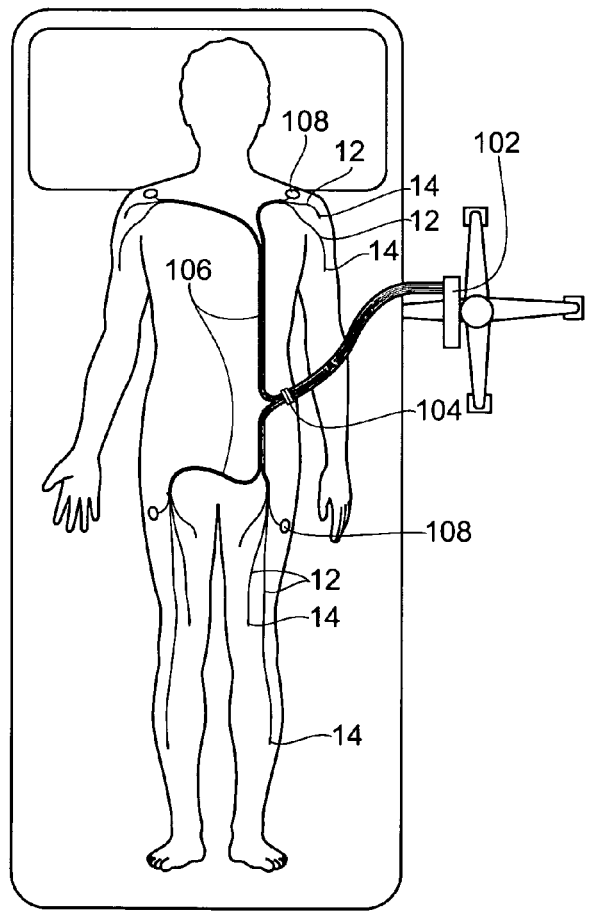
FIG. 21 is an anatomical view of the system shown in FIG. 20, showing the harnessed multi-channel neurostimulation assembly configured to be held on a movable stand next to the patient.

In an alternative embodiment of the neurostimulation system 54, the harnessed neurostimulation system 100 is able to provide coordinated stimulation of targeted muscles to induce isometric contractions in the muscles. As shown in FIGS. 20 and 21, the system 100 includes a multi-channel neurostimulation assembly 102. The neurostimulation assembly 102 is programmable as previously described, and includes the ability to program the coordinated stimulation between larger numbers of electrodes 14 strategically implanted throughout the body to provide the muscle conditioning. FIG. 20 shows the neurostimulation assembly 102 releasably secured to the patient's skin. FIG. 21 shows the neurostimulation system releasably secured to a portable stand positioned next to the patient.

The neurostimulation assembly 102 includes one or more connectors 104 to couple to one or more cable harnesses 106. The connector(s) 104 would take the place of the lead connector 27 shown in FIG. 1. The opposite end of the cable harness 106 then couples to the lead(s) 12 and electrode(s) 14. A return electrode 108 may also be included and coupled to the cable to provide a return path for the electrical stimulation in order to avoid inducing electrical currents near or across the heart.

As previously described, the neurostimulation system 100 also desirably includes a container 52 holding a prescribed number of replacement power sources 32, and instructions for use 56 that prescribe use of the neurostimulation assembly 102, including the periodic removal and replacement of a power source 32 with a fresh power source 32.

Figure 22:
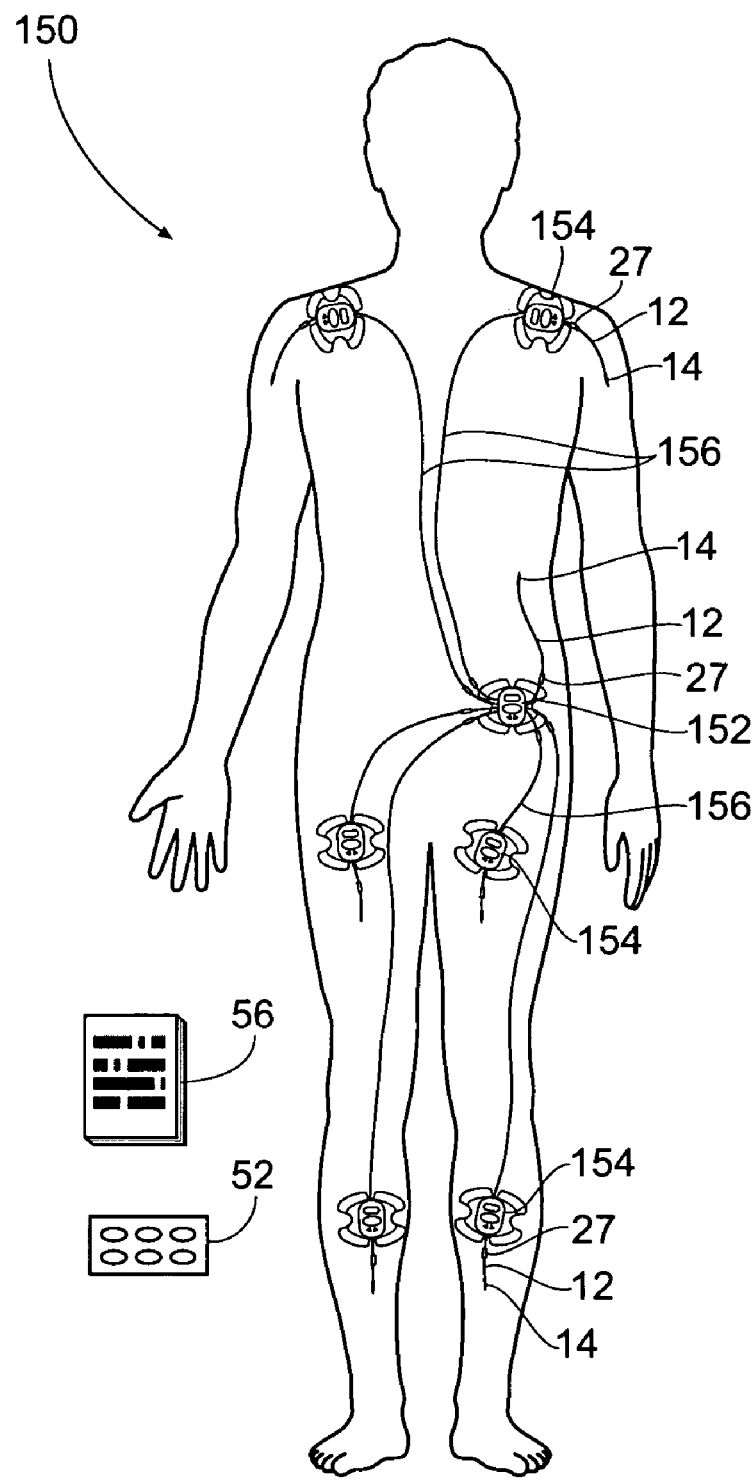
FIG. 22 is an anatomical view showing an additional alternative configuration of a neurostimulation assembly and system, the system including a master neurostimulation stimulation assembly and one or more slave neurostimulation assemblies, with the master assembly capable of providing coordinated control of multiple slave neurostimulation assemblies, the system capable of providing coordinated neurostimulation to multiple regions of the body.

FIG. 22 shows a coordinated stimulation system 150 similar to the system 100 shown in FIG. 20. The coordinated stimulation system 150 is adapted to provide coordinated stimulation of targeted muscles to induce isometric contractions. The neurostimulation assembly 152 is programmable as previously described, and includes the ability to program the coordinated stimulation between larger numbers of electrodes 14 strategically implanted throughout the body to provide the muscle conditioning.

The system 150 includes a master stimulation assembly 152 and a number of slave stimulation assemblies 154, and is also configurable as shown in FIG. 21, i.e., the master assembly 152 could be releasably coupled to a portable stand positioned next to the patient. Each slave assembly 154 could be electrically coupled to the master assembly 152 in series, or in parallel, as shown. The master assembly 152 is programmed to provide the coordination between each of the slave assemblies 154. The lead connector 27 provides connectivity to one or more system cables 156. In place of the cables 156, the master assembly 152 could use wireless telemetry to communicate with each slave assembly 154

Again as previously described, the neurostimulation system 150 also desirably includes a container 52 holding a prescribed number of replacement power sources 32, and instructions for use 56 that prescribe use of the neurostimulation assembly 102, including the periodic removal and replacement of a power source 32 with a fresh power source 32.

D. Continuous Active Motion (CAM)

CAM using the neurostimulation assembly 10 and/or neurostimulation system 54 provides the stimulus necessary to improve cardiovascular endurance, muscular strength, and neurologic coordination. Through the CAM, this active-assisted exercise is a technique used to assist the active, voluntary movement of the target limb, thereby decreasing the amount of strength needed to move the joints. This technique has been proven effective in increasing the strength of individuals beginning at very low levels. Therapeutic benefits include reduced inflammation of the affected joint, improved range of motion, pain relief, and enhanced functional mobility. CAM is differentiated from continuous passive motion (CPM), which is the movement of a joint or extremity through a range of motion without muscle contraction of the limb.

E. Post Trauma Anti-Scarring Treatment

Post surgical scarring, (e.g. posterior approaches to the spine), is the bane of most Orthopedic or Neurosurgical procedures. Scarring or adhesion, that is a fibrous band of scar tissue that binds together normally separate anatomical structures during the healing process, can be one of the single greatest reasons for patient's surgical "failure". A terrific and well executed operation by a gifted surgeon can be wasted in a short time due to the body's tendency to scar during post surgical healing. By applying the neurostimulation assembly 10 and/or neurostimulation system 54 to the muscles or nerves in the specific surgical wound area, relatively small motions may prevent scarring, while the tissue is healing.

F. Neuroplasticity Therapy

Individuals with neurological deficits, such as stroke survivors or those with multiple sclerosis may lose control of certain bodily functions. The brain, may, through a process called "neuroplasticity," recover functionally, by reorganizing the cortical maps or spinal cord-root interfaces and increasing auxiliary blood supply, which contributes to neurological recovery. By applying the neurostimulation assembly 10 and/or neurostimulation system 54 to affected areas of the body and providing excitation and input to the brain, a neuroplastic effect may occur, enabling the brain to re-learn and regain control of the lost function.

G. Anti-Spasm Therapy

The use of temporary neurotoxins (e.g. botox) has become widespread in treating severe muscles spasms from cerebral palsy, head injury, multiple sclerosis, and spinal cord injury to help improve walking, positioning and daily activities. Botox can also be used to treat eye conditions that cause the eye to cross or eyelid to blink continuously. It is also purported to eliminate wrinkles by relaxing small subcutaneous muscles. The neurostimulation assembly 10 and/or neurostimulation system 54 may be used as an alternative means of reducing the spasticity without having to temporarily paralyze the nerves and muscles. The neurostimulation assembly 10 and/or neurostimulation system 54 also may be useful in treating TMJ (temporomandibular joint) disorders, which are manifested by pain in the area of the jaw and associated muscles spasms and limitations in the ability to make the normal movements of speech, facial expression, eating, chewing, and swallowing.

H. Chronic or Temporary Pain Therapy

Localized pain in any area of the body can be treated with the neurostimulation assembly 10 and/or neurostimulation system 54 by applying it directly to the effected area. The neurostimulation assembly 10 and/or neurostimulation system 54 works by interfering with or blocking pain signals from reaching the brain.

I. Post-Surgical Reconditioning

Recovery of strength and muscle function following surgery can be promoted using the neurostimulation assembly 10 and/or neurostimulation system 54. The assembly 10 and/or system 54 can be prescribed post-operatively and installed in association with the appropriate muscles regions to provide a temporary regime of muscle stimulation, alone or in conjunction with a program of active movements, to aid an individual in recovering muscle tone, function, and conditioning following surgery.

J. Thromboembolism Prophyllaxis

The neurostimulation assembly 10 and/or neurostimulation system 54 can provide anti-thrombosis therapy by stimulating the leg muscles which increases venous return and prevent blood clots associated with pooling of blood in the lower extremities. Routine post-operative therapy is currently the use of pneumatic compression cuffs that the patients wear on their calves while in bed. The cuffs cycle and mechanically compress the calf muscles, thereby stimulating venous flow. Patients hate this, but every surgical bed in the hospital now has this unit attached to it. This same effect could be duplicated by installing a neurostimulation assembly 10. Prophylaxis is most effective if begun during surgery, as many, if not most clots, form during surgery. Thus, it is desirable to install a neurostimulation assembly 10 and begin use of the neurostimulation system 54 at the beginning of an operation.

K. Treatment of Osteoporosis

Cyclic muscle contraction loads bone sufficiently to prevent (and possibly) reverse osteoporosis. The effectiveness of such treatment is known to be frequency dependent. The neurostimulation assembly 10 and/or neurostimulation system 54 can be programmed to stimulate muscles at the appropriate frequency to prevent/reverse osteoporosis.

L. Neuroprosthesis

Restoration of lost motor due to a paralytic disease or injury can be achieved. The neurostimulation assembly 10 and/or neurostimulation system 54 can be controlled in real-time through an external control source, such as a heel switch monitoring gait. This external control source would trigger the neurostimulation system to become active for a pre-set period of time, enabling a functional movement in the lower or upper extremity of a person, thereby restoring the previously non-functioning paralyzed limb.

M. Body Sculpting

Muscular proportions of the human anatomy can be enhanced and their overall muscle definition may be modified by neurostimulation of a specific group of muscles. An example is stimulation of the abdominal region, increasing strength and improving muscle tone and definition. The neurostimulation assembly 10 and/or neurostimulation system 54 can be programmed to stimulate muscles at the appropriate frequency to change body physique and supplement the impact of active exercise.

Various features of the invention are set forth in the following claims.

We claim:

1. A neurostimulation assembly comprising
at least one electrode,
a carrier sized and configured to be worn by a user,
an electronics pod removably carried on-board the carrier, the electronics pod including circuitry configured to generate a stimulation pulse to the electrode, and
a power input bay carried on-board the electronics pod that is electrically coupled to the circuitry, the power input bay being sized and configured to accept a disposable power source, the power input bay also providing a communication interface configured to establish a programming link between the electronics pod and an external programming device.

2. An assembly according to claim 1
further including a disposable power source received into the power input bay, wherein the disposable power source includes circuitry adapted to electronically store information about the power source.

3. An assembly according to claim 2
wherein the power source circuitry includes non-volatile memory.

4. An assembly according to claim 1
further including a disposable power source received into the power input bay, wherein the electronics pod circuitry includes non-volatile memory and electronically stored information about the power source, wherein the electronically stored information is contained in the non-volatile memory.

5. An assembly according to claim 2
wherein the electronically stored information is selected from a group comprising power source usage data, a unique power source identification, and power source capacity.

6. An assembly according to claim 4
wherein the electronically stored information is selected from a group comprising power source usage data, a unique power source identification, and power source capacity.

7. An assembly according to claim 1
further including an adhesive region on the carrier adapted to temporarily secure the carrier to an external skin surface during use.

8. An assembly according to claim 7
the adhesive region further including a surface return electrode.

9. A neurostimulation assembly comprising
at least one electrode,
a carrier sized and configured to be worn by a user,
an electronics pod carried on-board the carrier, the electronics pod including circuitry configured to generate a stimulation pulse to the electrode, a user interface adapted to allow user input to the circuitry to adjust the stimulation pulse, and a visual output of neurostimulation assembly information, wherein the visual output is provided by an illumination source that illuminates at least a portion of the electronics pod, and
a power input bay carried on-board the carrier that is electrically coupled to the circuitry, the power input bay being sized and configured to hold a power source, the power input bay also providing a communication interface configured to establish a programming link between the circuitry and an external programming device.

* * * * *